US009487585B2

(12) United States Patent
Bachmann et al.

(10) Patent No.: US 9,487,585 B2
(45) Date of Patent: Nov. 8, 2016

(54) ANTIBODIES AGAINST 6-SULFO-LACNAC-POSITIVE HUMAN DENDRITIC CELLS, AND THEIR USE

(75) Inventors: Michael Bachmann, Kelkheim (DE); Daniel Gräfe, Dresden (DE)

(73) Assignee: Technische Universität Dresden, Dresden (DE)

( * ) Notice: Subject to any disclaimer, the term of this patent is extended or adjusted under 35 U.S.C. 154(b) by 675 days.

(21) Appl. No.: 13/814,512

(22) PCT Filed: Aug. 5, 2011

(86) PCT No.: PCT/EP2011/063545
§ 371 (c)(1),
(2), (4) Date: May 3, 2013

(87) PCT Pub. No.: WO2012/017085
PCT Pub. Date: Feb. 9, 2012

(65) Prior Publication Data
US 2015/0299312 A1    Oct. 22, 2015

(30) Foreign Application Priority Data

Aug. 6, 2010  (DE) .................. 10 2010 039 019

(51) Int. Cl.
| C12P 21/08 | (2006.01) |
| C07K 16/00 | (2006.01) |
| C07K 16/28 | (2006.01) |
| A61K 9/00 | (2006.01) |
| A61K 38/10 | (2006.01) |
| A61K 39/00 | (2006.01) |
| A61K 39/395 | (2006.01) |

(52) U.S. Cl.
CPC .............. *C07K 16/28* (2013.01); *A61K 9/0019* (2013.01); *A61K 38/10* (2013.01); *A61K 39/0011* (2013.01); *A61K 39/3955* (2013.01); *A61K 39/39533* (2013.01); *C07K 16/2896* (2013.01); *C07K 2317/31* (2013.01); *C07K 2317/34* (2013.01); *C07K 2317/565* (2013.01); *C07K 2317/622* (2013.01); *C07K 2317/626* (2013.01); *C07K 2317/92* (2013.01)

(58) Field of Classification Search
None
See application file for complete search history.

(56) References Cited

U.S. PATENT DOCUMENTS

2007/0014798 A1   1/2007  Rieber

FOREIGN PATENT DOCUMENTS

| EP | 1 078 060 B1 | 2/2001 |
| WO | 2009061996 A2 | 5/2009 |

OTHER PUBLICATIONS

Ong et al., 2009, PNAS, vol. 106: 4617-4622.*
Whisstock et al., 2003, Quart. Rev. Biophys. vol. 36: 307-340.*
Schwarzer A Ed: Herstellung und Charakterisierung rekombinanter Antikörper für eine adjuvante Immuntherapie PSCA-positiver Tumore; 1.6 Das Epitoppeptid des anti-La/SS-B Antikörpers 4B6 als potentielle Zielstruktur für bispezifische Antikörper; Jan. 1, 2006 pp. 22-24; pp. 96ff (see international search report: XP002662580).
Schäkel Knut et al.: 6-Sulfo LacNAc, a Novel Carbohydrate Modification of PSGL-1, Defines an Inflammatory Type of Human Dendritic Cells; Immunity, vol. 17, No. 3, pp. 289-301 (Sep. 2002) (see international search report); cited in specification, p. 2, second paragraph.
Schmitz Marc et al.: Tumoricidal Potential of Native Blood Dendritic Cells: Dierect Tumor Cell Killing and Activation of NK Cell-Mediated Cytotoxicity; Jorunal of Immunology; vol. 174, No. 7, pp. 4127-4134 (Apr. 1, 2005) (see international search report).
Schäkel K et al.: A novel dendritic cell population in human blood: one-step immunomagnetic isolation by a specific mAb (M-DC8) and in vitro priming of cytotoxic T lymphocytes; European Journal of Immunology; vol. 28, No. 12, pp. 4084-4093 (Dec. 1, 1998) (see international search report); cited in specification, p. 2, second paragraph.
Mende Ines et al.: Highly efficient antigen targeting to M-DC8+ dendritic cells via FC(gamma)RIII/CD16-specific antibody conjugates; International Immunology; vol. 17. No. 5, pp. 539-547 (May 2005) (see international search report).
Schäkel K et al.: Human 6-sulfo LacNAc-expressing dendritic cells are principal producers of early interleukin-12 and are controlled by erythrocytes; Immunity, vol. 24, No. 6, pp. 7676-77 (Jun. 2006) (see international search report); cited in specification, p. 2, second paragraph.
Bippes C C et al.: A Novel Modular Antigen Delivery System for Immuno Targeting of Human 6-Sulfo LacNAc-Positive Blood Dendritic Cells (SlanDCs); PLOS ONE, vol. 6, No. 1, pp. e16315 (Jan. 1, 2011) (see international search report).

(Continued)

*Primary Examiner* — Amy Juedes
(74) *Attorney, Agent, or Firm* — Gudrun E. Huckett

(57) ABSTRACT

The invention relates to a composition which contains at least one anti-slan antibody and to its diagnostic and therapeutic use. The composition according to the invention comprises: a) at least one anti-slan antibody, b) at least one binding unit which binds to a co-stimulus binding to a co-stimulus-specific receptor on dendritic cells, thereby bringing about the modulation, preferably the activation, of said dendritic cells, and c) at least one antigen. The invention furthermore comprises anti-slan antibodies which include CDRs with the following sequences: variable region of the heavy chain: CDR1 (SEQ ID No. 1), CDR2 (SEQ ID No. 2), where Xaa is selected from among M, L, F, or I, preferably from among M or I, CDR3 (SEQ ID No. 5) and variable region of the light chain: CDR1 (SEQ ID No. 6), where Xaa is selected from among S, T, N, Q, H, K or R, preferably from among S or N, CDR2 (SEQ ID No. 9) and CDR3 (SEQ ID No. 10).

14 Claims, 9 Drawing Sheets

(56) References Cited

OTHER PUBLICATIONS

De Baey Annegret et al: Phenotype and function of human dendritic cells derived from M-DC8+ monocytes; European Journal of Immunology, vol. 31, No. 6, pp. 1646-1655 (Jun. 2001) (see international search report).

Birkholz Katrin et al.: Targeting of DEC-205 on human dendritic cells results in efficient MHC class II restricted antigen presentation; Blood, vol. 116, No. 13, pp. 2277-2285 (Jun. 21, 2010) (see international search report).

Wehner Rebekka et al.: Reciprocal activating interaction between 6-sulfo LacNAc dendritic cells and NK cells; Int. J. Cancer: 124, 358-366 (2009)—cited in specification, p. 2, second paragraph.

Janeway, Immunologie (7th edition 2009) chapter 7.26, p. 385; cited in specification, p. 1, fourth paragraph.

* cited by examiner

A

B

C

SEQUENCE LISTING

<160> NUMBER OF SEQ ID NOS: 55

<210> SEQ ID NO 1
<211> LENGTH: 5
<212> TYPE: PRT
<213> ORGANISM: Mus musculus

<400> SEQUENCE: 1

Thr Tyr Gly Val His
1               5

<210> SEQ ID NO 2
<211> LENGTH: 16
<212> TYPE: PRT
<213> ORGANISM: Mus musculus
<220> FEATURE:
<221> NAME/KEY: misc_feature
<222> LOCATION: (15)..(15)
<223> OTHER INFORMATION: Xaa can be any naturally occurring amino acid

<400> SEQUENCE: 2

Val Ile Trp Ser Gly Gly Gly Thr Asp Phe Asn Val Ala Phe Xaa Ser
1               5                   10                  15

<210> SEQ ID NO 3
<211> LENGTH: 16
<212> TYPE: PRT
<213> ORGANISM: Mus musculus

<400> SEQUENCE: 3

Val Ile Trp Ser Gly Gly Gly Thr Asp Phe Asn Val Ala Phe Met Ser
1               5                   10                  15

<210> SEQ ID NO 4
<211> LENGTH: 16
<212> TYPE: PRT
<213> ORGANISM: Mus musculus

<400> SEQUENCE: 4

Val Ile Trp Ser Gly Gly Gly Thr Asp Phe Asn Val Ala Phe Ile Ser
1               5                   10                  15

<210> SEQ ID NO 5
<211> LENGTH: 12
<212> TYPE: PRT
<213> ORGANISM: Mus musculus

<400> SEQUENCE: 5

Arg Thr Thr Asn Asp Gly Asn Tyr Ala Phe Ala Tyr
1               5                   10

<210> SEQ ID NO 6
<211> LENGTH: 16
<212> TYPE: PRT
<213> ORGANISM: Mus musculus
<220> FEATURE:
<221> NAME/KEY: misc_feature
<222> LOCATION: (12)..(12)
<223> OTHER INFORMATION: Xaa can be any naturally occurring amino acid

<400> SEQUENCE: 6

Arg Ser Ser Gln Asn Ile Leu His Ser Asp Gly Xaa Thr Tyr Leu Glu
1               5                   10                  15

<210> SEQ ID NO 7
<211> LENGTH: 16

```
<212> TYPE: PRT
<213> ORGANISM: Mus musculus

<400> SEQUENCE: 7

Arg Ser Ser Gln Asn Ile Leu His Ser Asp Gly Ser Thr Tyr Leu Glu
1               5                   10                  15

<210> SEQ ID NO 8
<211> LENGTH: 16
<212> TYPE: PRT
<213> ORGANISM: Mus musculus

<400> SEQUENCE: 8

Arg Ser Ser Gln Asn Ile Leu His Ser Asp Gly Asn Thr Tyr Leu Glu
1               5                   10                  15

<210> SEQ ID NO 9
<211> LENGTH: 7
<212> TYPE: PRT
<213> ORGANISM: Mus musculus

<400> SEQUENCE: 9

Lys Val Ser Asn Arg Phe Ser
1               5

<210> SEQ ID NO 10
<211> LENGTH: 9
<212> TYPE: PRT
<213> ORGANISM: Mus musculus

<400> SEQUENCE: 10

Phe Gln Gly Ser His Val Pro Trp Thr
1               5

<210> SEQ ID NO 11
<211> LENGTH: 357
<212> TYPE: DNA
<213> ORGANISM: Mus musculus

<400> SEQUENCE: 11
gaggtcaagc tgcaggagtc aggacctggc ctagtgcagc cctcacagag cctgtccatc        60
acctgcacag tctctggttt ctcattaact acctatggtg tacactggat tcgccagtct       120
ccaggaaagg gtctggagtg gctgggagtg atatggagtg gtggaggtac tgactttaat       180
gtagctttca tgtccagact gagcatcaac aaggacaatt ccaagagcca aattttcttt       240
aaaatgaaca gtctgcaagc taatgacaca gccatatatt attgtgccag aagaacgacc       300
aacgatggta actacgcttt tgcttattgg ggccaaggga ctctggtcac tgtctct          357

<210> SEQ ID NO 12
<211> LENGTH: 119
<212> TYPE: PRT
<213> ORGANISM: Mus musculus

<400> SEQUENCE: 12

Glu Val Lys Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Ile Arg Gln Ser Pro Gly Lys Gly Leu Glu Trp Leu
        35                  40                  45

Gly Val Ile Trp Ser Gly Gly Gly Thr Asp Phe Asn Val Ala Phe Met
```

```
                    50                  55                  60
Ser Arg Leu Ser Ile Asn Lys Asp Asn Ser Lys Ser Gln Ile Phe Phe
 65                  70                  75                  80

Lys Met Asn Ser Leu Gln Ala Asn Asp Thr Ala Ile Tyr Tyr Cys Ala
                 85                  90                  95

Arg Arg Thr Thr Asn Asp Gly Asn Tyr Ala Phe Ala Tyr Trp Gly Gln
            100                 105                 110

Gly Thr Leu Val Thr Val Ser
        115
```

<210> SEQ ID NO 13
<211> LENGTH: 363
<212> TYPE: DNA
<213> ORGANISM: Mus musculus

<400> SEQUENCE: 13

```
gatattgtga tgacacagtc tccactctcc ctgcctgtca gtcttggaga tcaagcctcc    60
atctcttgca gatctagtca gaacatttta catagtgatg gaagcaccta tttagaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcagggttc acatgttccg   300
tggacgttcg gtggaggcac caagctggaa atcaaacggg ctgatgctgc accaactgta   360
tcc                                                                 363
```

<210> SEQ ID NO 14
<211> LENGTH: 121
<212> TYPE: PRT
<213> ORGANISM: Mus musculus

<400> SEQUENCE: 14

```
Asp Ile Val Met Thr Gln Ser Pro Leu Ser Leu Pro Val Ser Leu Gly
  1               5                  10                  15

Asp Gln Ala Ser Ile Ser Cys Arg Ser Ser Gln Asn Ile Leu His Ser
                 20                  25                  30

Asp Gly Ser Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
            100                 105                 110

Arg Ala Asp Ala Ala Pro Thr Val Ser
        115                 120
```

<210> SEQ ID NO 15
<211> LENGTH: 357
<212> TYPE: DNA
<213> ORGANISM: Mus musculus

<400> SEQUENCE: 15

```
gaagtcaagc tggagcagtc aggacctggc ctagtgcagc tctcacagag cctgtccatc    60
acctgcacag tctctggttt ctcattaact acctatggtg tacactggat tcgccagtct   120
```

```
ccaggaaagg gtctggagtg gctgggagtg atatggagtg gtggaggtac tgactttaat    180
gtagctttca tatccagact gagcatcaac aaggacaatt ccaagagcca agttttcttt    240
aaaatgaaca gtctgcaagc taatgacaca gccatatatt actgtgccag aagaacgacc    300
aacgatggta actacgcttt tgcttactgg ggccaaggga ctctggtcac tgtctct       357
```

<210> SEQ ID NO 16
<211> LENGTH: 119
<212> TYPE: PRT
<213> ORGANISM: Mus musculus

<400> SEQUENCE: 16

```
Glu Val Lys Leu Glu Gln Ser Gly Pro Gly Leu Val Gln Leu Ser Gln
1               5                   10                  15

Ser Leu Ser Ile Thr Cys Thr Val Ser Gly Phe Ser Leu Thr Thr Tyr
            20                  25                  30

Gly Val His Trp Ile Arg Gln Ser Pro Gly Lys Gly Leu Glu Trp Leu
        35                  40                  45

Gly Val Ile Trp Ser Gly Gly Thr Asp Phe Asn Val Ala Phe Ile
    50                  55                  60

Ser Arg Leu Ser Ile Asn Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Arg Thr Thr Asn Asp Gly Asn Tyr Ala Phe Ala Tyr Trp Gly Gln
            100                 105                 110

Gly Thr Leu Val Thr Val Ser
        115
```

<210> SEQ ID NO 17
<211> LENGTH: 363
<212> TYPE: DNA
<213> ORGANISM: Mus musculus

<400> SEQUENCE: 17

```
gatattgtga tgacacagtc tccactctcc ctgcctgtca gtcttggaga tcaagcctcc     60
atctcttgca gatctagtca gaacatttta catagtgatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtga aggctgagga tctgggagtt tattactgct ttcaaggttc acatgttccg    300
tggacgttcg gtggaggcac caagctggaa atcaaacggg ctgatgctgc accaactgta    360
tcc                                                                  363
```

<210> SEQ ID NO 18
<211> LENGTH: 121
<212> TYPE: PRT
<213> ORGANISM: Mus musculus

<400> SEQUENCE: 18

```
Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Asn Ile Leu His Ser
            20                  25                  30

Asp Gly Asn Thr Tyr Leu Glu Trp Tyr Leu Gln Lys Pro Gly Gln Ser
        35                  40                  45
```

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
                100                 105                 110

Arg Ala Asp Ala Ala Pro Thr Val Ser
            115                 120

<210> SEQ ID NO 19
<211> LENGTH: 130
<212> TYPE: PRT
<213> ORGANISM: Mus musculus

<400> SEQUENCE: 19

Met Ala Asp Tyr Lys Gln Val Lys Leu Gln Gln Ser Gly Ala Glu Leu
  1               5                  10                  15

Val Lys Pro Gly Ala Ser Val Lys Leu Ser Cys Lys Ala Ser Gly Tyr
                 20                  25                  30

Thr Phe Thr Thr Tyr Tyr Met Tyr Trp Val Lys Gln Arg Pro Gly Gln
             35                  40                  45

Gly Leu Glu Trp Ile Gly Glu Ile Ser Pro Ile Asn Gly Ala Thr Asn
     50                  55                  60

Phe Asn Glu Lys Phe Lys Ser Lys Ala Thr Leu Thr Val Asp Lys Ser
 65                  70                  75                  80

Ser Ser Thr Ala Tyr Met Gln Leu Ser Ser Leu Thr Ser Glu Asp Ser
                 85                  90                  95

Ala Val Tyr Tyr Cys Thr Thr Leu Gly Glu Lys Gly Phe Ala Tyr Trp
                100                 105                 110

Gly Gln Gly Thr Leu Val Thr Val Ser Ala Glu Ser Gln Ser Phe Pro
            115                 120                 125

Asn Val
    130

<210> SEQ ID NO 20
<211> LENGTH: 121
<212> TYPE: PRT
<213> ORGANISM: Mus musculus

<400> SEQUENCE: 20

Asp Ile Val Leu Thr Gln Ser Pro Leu Ser Leu Pro Val Ser Leu Gly
  1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
                100                 105                 110

```
Arg Ala Asp Ala Ala Pro Thr Val Ser
        115                 120

<210> SEQ ID NO 21
<211> LENGTH: 114
<212> TYPE: PRT
<213> ORGANISM: Mus musculus

<400> SEQUENCE: 21

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Leu Thr Ser Tyr
            20                  25                  30

Trp Leu His Trp Val Lys Gln Trp Pro Gly Arg Gly Leu Glu Trp Ile
        35                  40                  45

Gly Arg Ile Asp Pro Asn Ser Gly Thr Lys Tyr Asp Glu Lys Phe
    50                  55                  60

Lys Ser Lys Ala Thr Leu Thr Val Asp Lys Pro Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Trp Asp Tyr Trp Gly Gly Ile Asn Gly Thr Thr Val Thr Val
            100                 105                 110

Ser Ser

<210> SEQ ID NO 22
<211> LENGTH: 110
<212> TYPE: PRT
<213> ORGANISM: Mus musculus

<400> SEQUENCE: 22

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gly Ile Asn Gln Tyr Ser Gly
            85                  90                  95

Tyr Pro Tyr Thr Phe Gly Gly Gly Thr Lys Leu Glu Ile Lys
            100                 105                 110

<210> SEQ ID NO 23
<211> LENGTH: 18
<212> TYPE: PRT
<213> ORGANISM: Homo sapiens

<400> SEQUENCE: 23

Glu Lys Glu Ala Leu Lys Lys Ile Ile Glu Asp Gln Gln Glu Ser Leu
1               5                   10                  15

Asn Lys

<210> SEQ ID NO 24
```

```
<211> LENGTH: 42
<212> TYPE: PRT
<213> ORGANISM: Homo sapiens

<400> SEQUENCE: 24

Trp Glu Val Leu Glu Gly Glu Val Lys Glu Ala Leu Lys Lys Ile
1               5                   10                  15

Ile Glu Asp Gln Gln Glu Ser Leu Asn Lys Trp Lys Ser Lys Gly Arg
                20                  25                  30

Arg Phe Lys Gly Lys Gly Lys Gly Asn Lys
            35                  40

<210> SEQ ID NO 25
<211> LENGTH: 408
<212> TYPE: PRT
<213> ORGANISM: Homo sapiens

<400> SEQUENCE: 25

Met Ala Glu Asn Gly Asp Asn Glu Lys Met Ala Ala Leu Glu Ala Lys
1               5                   10                  15

Ile Cys His Gln Ile Glu Tyr Tyr Phe Gly Asp Phe Asn Leu Pro Arg
                20                  25                  30

Asp Lys Phe Leu Lys Glu Gln Ile Lys Leu Asp Glu Gly Trp Val Pro
            35                  40                  45

Leu Glu Ile Met Ile Lys Phe Asn Arg Leu Asn Arg Leu Thr Thr Asp
50                  55                  60

Phe Asn Val Ile Val Glu Ala Leu Ser Lys Ser Lys Ala Glu Leu Met
65                  70                  75                  80

Glu Ile Ser Glu Asp Lys Thr Lys Ile Arg Arg Ser Pro Ser Lys Pro
                85                  90                  95

Leu Pro Glu Val Thr Asp Glu Tyr Lys Asn Asp Val Lys Asn Arg Ser
            100                 105                 110

Val Tyr Ile Lys Gly Phe Pro Thr Asp Ala Thr Leu Asp Asp Ile Lys
        115                 120                 125

Glu Trp Leu Glu Asp Lys Gly Gln Val Leu Asn Ile Gln Met Arg Arg
130                 135                 140

Thr Leu His Lys Ala Phe Lys Gly Ser Ile Phe Val Val Phe Asp Ser
145                 150                 155                 160

Ile Glu Ser Ala Lys Lys Phe Val Glu Thr Pro Gly Gln Lys Tyr Lys
                165                 170                 175

Glu Thr Asp Leu Leu Ile Leu Phe Lys Asp Asp Tyr Phe Ala Lys Lys
            180                 185                 190

Asn Glu Glu Arg Lys Gln Asn Lys Val Glu Ala Lys Leu Arg Ala Lys
        195                 200                 205

Gln Glu Gln Glu Ala Lys Gln Lys Leu Glu Glu Asp Ala Glu Met Lys
    210                 215                 220

Ser Leu Glu Glu Lys Ile Gly Cys Leu Leu Lys Phe Ser Gly Asp Leu
225                 230                 235                 240

Asp Asp Gln Thr Cys Arg Glu Asp Leu His Ile Leu Phe Ser Asn His
                245                 250                 255

Gly Glu Ile Lys Trp Ile Asp Phe Val Arg Gly Ala Lys Glu Gly Ile
            260                 265                 270

Ile Leu Phe Lys Glu Lys Ala Lys Glu Ala Leu Gly Lys Ala Lys Asp
        275                 280                 285

Ala Asn Asn Gly Asn Leu Gln Leu Arg Asn Lys Glu Val Thr Trp Glu
    290                 295                 300
```

-continued

Val Leu Glu Gly Glu Val Lys Glu Ala Leu Lys Lys Ile Ile Glu
305                 310                 315                 320

Asp Gln Gln Glu Ser Leu Asn Lys Trp Lys Ser Lys Gly Arg Arg Phe
            325                 330                 335

Lys Gly Lys Gly Lys Gly Asn Lys Ala Ala Gln Pro Gly Ser Gly Lys
        340                 345                 350

Gly Lys Val Gln Phe Gln Gly Lys Lys Thr Lys Phe Ala Ser Asp Asp
    355                 360                 365

Glu His Asp Glu His Asp Glu Asn Gly Ala Thr Gly Pro Val Lys Arg
370                 375                 380

Ala Arg Glu Glu Thr Asp Lys Glu Glu Pro Ala Ser Lys Gln Gln Lys
385                 390                 395                 400

Thr Glu Asn Gly Ala Gly Asp Gln
            405

<210> SEQ ID NO 26
<211> LENGTH: 5
<212> TYPE: PRT
<213> ORGANISM: Mus musculus

<400> SEQUENCE: 26

Asp Phe Trp Met Asn
1               5

<210> SEQ ID NO 27
<211> LENGTH: 19
<212> TYPE: PRT
<213> ORGANISM: Mus musculus

<400> SEQUENCE: 27

Gln Ile Arg Asn Lys Pro Asn Asn Tyr Glu Thr Tyr Tyr Ser Asp Ser
1               5                   10                  15

Leu Lys Gly

<210> SEQ ID NO 28
<211> LENGTH: 8
<212> TYPE: PRT
<213> ORGANISM: Mus musculus

<400> SEQUENCE: 28

Leu Gly Asn Ser Trp Phe Ala Tyr
1               5

<210> SEQ ID NO 29
<211> LENGTH: 17
<212> TYPE: PRT
<213> ORGANISM: Mus musculus

<400> SEQUENCE: 29

Arg Ser Ser Gln Ser Leu Leu Asp Ser Arg Thr Arg Lys Asn Tyr Leu
1               5                   10                  15

Ala

<210> SEQ ID NO 30
<211> LENGTH: 7
<212> TYPE: PRT
<213> ORGANISM: Mus musculus

<400> SEQUENCE: 30

Trp Ala Ser Thr Arg Glu Ser

```
<210> SEQ ID NO 31
<211> LENGTH: 8
<212> TYPE: PRT
<213> ORGANISM: Mus musculus

<400> SEQUENCE: 31

Lys Gln Ser Tyr Asn Leu Pro Thr
1               5

<210> SEQ ID NO 32
<211> LENGTH: 1758
<212> TYPE: DNA
<213> ORGANISM: Artificial Sequence
<220> FEATURE:
<223> OTHER INFORMATION: Fusion protein

<400> SEQUENCE: 32
atggagacag acacactcct gctatgggta ctgctgctct ggttccagg ttccactggt      60
gacgcggccc agccggccat ggcggactac aaacaggtta agctgcagca gtctggggct    120
gaattggtga agcctggggc ttcagtgaag ttgtcctgca aggcttctgg ctacaccttc    180
accacctact atatgtactg ggtgaagcag aggcctggac aaggccttga atggattgga    240
gagattagtc ctataaatgg tgctactaac ttcaatgaga agttcaagag caaggccaca    300
ctgactgtag acaaatcctc cagcacagca tacatgcaac tcagcagcct gacatctgag    360
gactctgcgg tctattactg tacaaactgg ggagagaagg ttttgcttta ctggggccaa    420
gggactctgg tcactgtctc tgcagagagt cagtccttcc caaatgtcgg tggtggtgga    480
tccgacattg tgctcacaca gtctccatcc tccctggctg tgtcagcagg agagaaggtc    540
actatgagct gcagatccag tcagagtctg ctcgacagta gaacccgaaa gaactacttg    600
gcttggtacc agcagaaacc agggcagtct cctaaactgc tgatctactg ggcatccact    660
agggaatctg gggtccctga tcgcttcaca ggcagtggat ctgggacaga tttcactctc    720
accatcagca atgtgcaggc tgaagacctg cagtttatt actgcaagca atcttataat    780
cttccgacgt tcggtggagg caccaagctg gaaatcaaac gggctgatgc tgcaccaact    840
gtatccgggc ccgtggtgg tggttctggt ggtggtggtt ctggcgccgg cggctccggt    900
ggtggtggtt ccggtggtgg tggctccatg gcggactaca agaggtcaa gctgcaggag    960
tcaggaggag gcttggtgca acctgggagg cccatgaaac tctcctgtgt tgcctctgga   1020
ttcacttta gtgacttctg gatgaactgg gtccgccagt ctccagagaa aggactggag   1080
tgggtagcac aaattagaaa caaacctaat aattatgaaa cgtattattc agattctttg   1140
aaaggcagat tcaccatctc aagagatgat tccaaaagta gtgtctacct gcaaatgaac   1200
aacttaagac ctgaagacat gggtatctat tactgtacac taggtaactc ctggtttgct   1260
tactggggcc aagggactct ggtcactgtc tctggtggtg gtggatccga cattgtgctg   1320
acccagtctc cactctccct gcctgtcagt cttggagatc aagcctccat ctcttgcaga   1380
tctagtcaga gccttgtaca cagtaatgga aacacctatt acattggta cctgcagaag   1440
ccaggccagt ctccaaagct cctgatctac aaagtttcca accgattttc tggggtccca   1500
gacaggttca gtggcagtgg atcagggaca gatttcacac tcaagatcag cagagtggag   1560
gctgaggatc tgggagtta tttctgctct caaagtacac atgttccatt cacgttcggc   1620
tcggggacaa agttggaaat aaaacgggct gatgctgcac caactgtatc cgcggccgct   1680
```

```
cgaggagggc ccgaacaaaa actcatctca gaagaggatc tgaatagcgc cgtcgaccat   1740
catcatcatc atcattga                                                 1758
```

<210> SEQ ID NO 33
<211> LENGTH: 585
<212> TYPE: PRT
<213> ORGANISM: Artificial Sequence
<220> FEATURE:
<223> OTHER INFORMATION: Fusion protein

<400> SEQUENCE: 33

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Asp Tyr Lys Gln
            20                  25                  30

Val Lys Leu Gln Gln Ser Gly Ala Glu Leu Val Lys Pro Gly Ala Ser
        35                  40                  45

Val Lys Leu Ser Cys Lys Ala Ser Gly Tyr Thr Phe Thr Thr Tyr Tyr
    50                  55                  60

Met Tyr Trp Val Lys Gln Arg Pro Gly Gln Gly Leu Glu Trp Ile Gly
65                  70                  75                  80

Glu Ile Ser Pro Ile Asn Gly Ala Thr Asn Phe Asn Glu Lys Phe Lys
                85                  90                  95

Ser Lys Ala Thr Leu Thr Val Asp Lys Ser Ser Ser Thr Ala Tyr Met
            100                 105                 110

Gln Leu Ser Ser Leu Thr Ser Glu Asp Ser Ala Val Tyr Tyr Cys Thr
        115                 120                 125

Thr Leu Gly Glu Lys Gly Phe Ala Tyr Trp Gly Gln Gly Thr Leu Val
    130                 135                 140

Thr Val Ser Ala Glu Ser Gln Ser Phe Pro Asn Val Gly Gly Gly Gly
145                 150                 155                 160

Ser Asp Ile Val Leu Thr Gln Ser Pro Ser Ser Leu Ala Val Ser Ala
                165                 170                 175

Gly Glu Lys Val Thr Met Ser Cys Arg Ser Ser Gln Ser Leu Leu Asp
            180                 185                 190

Ser Arg Thr Arg Lys Asn Tyr Leu Ala Trp Tyr Gln Gln Lys Pro Gly
        195                 200                 205

Gln Ser Pro Lys Leu Leu Ile Tyr Trp Ala Ser Thr Arg Glu Ser Gly
    210                 215                 220

Val Pro Asp Arg Phe Thr Gly Ser Gly Ser Gly Thr Asp Phe Thr Leu
225                 230                 235                 240

Thr Ile Ser Asn Val Gln Ala Glu Asp Leu Ala Val Tyr Tyr Cys Lys
                245                 250                 255

Gln Ser Tyr Asn Leu Pro Thr Phe Gly Gly Gly Thr Lys Leu Glu Ile
            260                 265                 270

Lys Arg Ala Asp Ala Ala Pro Thr Val Ser Gly Pro Gly Gly Gly Gly
        275                 280                 285

Ser Gly Gly Gly Gly Ser Gly Ala Gly Gly Ser Gly Gly Gly Gly Ser
    290                 295                 300

Gly Gly Gly Gly Ser Met Ala Asp Tyr Lys Glu Val Lys Leu Gln Glu
305                 310                 315                 320

Ser Gly Gly Gly Leu Val Gln Pro Gly Arg Pro Met Lys Leu Ser Cys
                325                 330                 335

Val Ala Ser Gly Phe Thr Phe Ser Asp Phe Trp Met Asn Trp Val Arg
            340                 345                 350
```

```
Gln Ser Pro Glu Lys Gly Leu Glu Trp Val Ala Gln Ile Arg Asn Lys
        355                 360                 365
Pro Asn Asn Tyr Glu Thr Tyr Tyr Ser Asp Ser Leu Lys Gly Arg Phe
    370                 375                 380
Thr Ile Ser Arg Asp Asp Ser Lys Ser Ser Val Tyr Leu Gln Met Asn
385                 390                 395                 400
Asn Leu Arg Pro Glu Asp Met Gly Ile Tyr Tyr Cys Thr Leu Gly Asn
                405                 410                 415
Ser Trp Phe Ala Tyr Trp Gly Gln Gly Thr Leu Val Thr Val Ser Gly
            420                 425                 430
Gly Gly Gly Ser Asp Ile Val Leu Thr Gln Ser Pro Leu Ser Leu Pro
        435                 440                 445
Val Ser Leu Gly Asp Gln Ala Ser Ile Ser Cys Arg Ser Ser Gln Ser
    450                 455                 460
Leu Val His Ser Asn Gly Asn Thr Tyr Leu His Trp Tyr Leu Gln Lys
465                 470                 475                 480
Pro Gly Gln Ser Pro Lys Leu Leu Ile Tyr Lys Val Ser Asn Arg Phe
                485                 490                 495
Ser Gly Val Pro Asp Arg Phe Ser Gly Ser Gly Ser Gly Thr Asp Phe
            500                 505                 510
Thr Leu Lys Ile Ser Arg Val Glu Ala Glu Asp Leu Gly Val Tyr Phe
        515                 520                 525
Cys Ser Gln Ser Thr His Val Pro Phe Thr Phe Gly Ser Gly Thr Lys
    530                 535                 540
Leu Glu Ile Lys Arg Ala Asp Ala Ala Pro Thr Val Ser Ala Ala Ala
545                 550                 555                 560
Arg Gly Gly Pro Glu Gln Lys Leu Ile Ser Glu Glu Asp Leu Asn Ser
                565                 570                 575
Ala Val Asp His His His His His His
            580                 585

<210> SEQ ID NO 34
<211> LENGTH: 1113
<212> TYPE: DNA
<213> ORGANISM: Artificial Sequence
<220> FEATURE:
<223> OTHER INFORMATION: Fusion protein

<400> SEQUENCE: 34
atgggcagca gccatcatca tcatcatcac agcagcggcc tggtgccgcg cggcagccat      60
atggctagcg agaaagaagc actgaagaaa ataatagaag accaacaaga atccctaaac     120
aaaactagca tgactggtgg acagcaaatg ggtcgggatc cgagacgaaa ttattctctt     180
gataaaatta ttgttgatta taatcttcaa tctaaaatta ctcttcctcg taggaagctt     240
gcggccgcac tcgagaaaga agcactgaag aaaataatag agaccaaca agaatcccta     300 aacaaaacta gggacgtcat ggtgagcaag ggcgaggagc tgttcaccgg ggtggtgccc     360
atcctggtcg agctggacgg cgacgtaaac ggccacaagt tcagcgtgtc cggcgagggc     420
gagggcgatg ccacctacgg caagctgacc ctgaagttca tctgcaccac cggcaagctg     480
cccgtgccct ggcccaccct cgtgaccacc ctgacctacg gcgtgcagtg cttcagccgc     540
taccccgacc acatgaagca gcacgacttc ttcaagtccg ccatgcccga aggctacgtc     600
caggagcgca ccatcttctt caaggacgac ggcaactaca agacccgcgc cgaggtgaag     660
ttcgagggcg acaccctggt gaaccgcatc gagctgaagg gcatcgactt caaggaggac     720
```

```
ggcaacatcc tgggggcacaa gctggagtac aactacaaca gccacaacgt ctatatcatg    780
gccgacaagc agaagaacgg catcaaggtg aacttcaaga tccgccacaa catcgaggac    840
ggcagcgtgc agctcgccga ccactaccag cagaacaccc ccatcggcga cggccccgtg    900
ctgctgcccg acaaccacta cctgagcacc cagtccgccc tgagcaaaga ccccaacgag    960
aagcgcgatc acatggtcct gctggagttc gtgaccgccg ccgggatcac tctcggcatg   1020
gacgtcagta ctgagaaaga agcactgaag aaaataatag aagaccaaca agaatcccta   1080
aacaaaacta gtcaccacca ccaccaccac tga                                1113
```

<210> SEQ ID NO 35
<211> LENGTH: 370
<212> TYPE: PRT
<213> ORGANISM: Artificial Sequence
<220> FEATURE:
<223> OTHER INFORMATION: Fusion protein

<400> SEQUENCE: 35

```
Met Gly Ser Ser His His His His His Ser Ser Gly Leu Val Pro
 1               5                  10                  15

Arg Gly Ser His Met Ala Ser Glu Lys Glu Ala Leu Lys Lys Ile Ile
            20                  25                  30

Glu Asp Gln Gln Glu Ser Leu Asn Lys Thr Ser Met Thr Gly Gly Gln
        35                  40                  45

Gln Met Gly Arg Asp Pro Arg Arg Asn Tyr Ser Leu Asp Lys Ile Ile
    50                  55                  60

Val Asp Tyr Asn Leu Gln Ser Lys Ile Thr Leu Pro Arg Arg Lys Leu
65                  70                  75                  80

Ala Ala Ala Leu Glu Lys Glu Ala Leu Lys Lys Ile Ile Glu Asp Gln
                85                  90                  95

Gln Glu Ser Leu Asn Lys Thr Arg Asp Val Met Val Ser Lys Gly Glu
            100                 105                 110

Glu Leu Phe Thr Gly Val Val Pro Ile Leu Val Glu Leu Asp Gly Asp
        115                 120                 125

Val Asn Gly His Lys Phe Ser Val Ser Gly Glu Gly Glu Gly Asp Ala
    130                 135                 140

Thr Tyr Gly Lys Leu Thr Leu Lys Phe Ile Cys Thr Thr Gly Lys Leu
145                 150                 155                 160

Pro Val Pro Trp Pro Thr Leu Val Thr Thr Leu Thr Tyr Gly Val Gln
                165                 170                 175

Cys Phe Ser Arg Tyr Pro Asp His Met Lys Gln His Asp Phe Phe Lys
            180                 185                 190

Ser Ala Met Pro Glu Gly Tyr Val Gln Glu Arg Thr Ile Phe Phe Lys
        195                 200                 205

Asp Asp Gly Asn Tyr Lys Thr Arg Ala Glu Val Lys Phe Glu Gly Asp
    210                 215                 220

Thr Leu Val Asn Arg Ile Glu Leu Lys Gly Ile Asp Phe Lys Glu Asp
225                 230                 235                 240

Gly Asn Ile Leu Gly His Lys Leu Glu Tyr Asn Tyr Asn Ser His Asn
                245                 250                 255

Val Tyr Ile Met Ala Asp Lys Gln Lys Asn Gly Ile Lys Val Asn Phe
            260                 265                 270

Lys Ile Arg His Asn Ile Glu Asp Gly Ser Val Gln Leu Ala Asp His
        275                 280                 285
```

Tyr Gln Gln Asn Thr Pro Ile Gly Asp Gly Pro Val Leu Leu Pro Asp
            290                 295                 300

Asn His Tyr Leu Ser Thr Gln Ser Ala Leu Ser Lys Asp Pro Asn Glu
305                 310                 315                 320

Lys Arg Asp His Met Val Leu Leu Glu Phe Val Thr Ala Ala Gly Ile
                325                 330                 335

Thr Leu Gly Met Asp Val Ser Thr Glu Lys Glu Ala Leu Lys Lys Ile
                340                 345                 350

Ile Glu Asp Gln Gln Glu Ser Leu Asn Lys Thr Ser His His His His
            355                 360                 365

His His
   370

<210> SEQ ID NO 36
<211> LENGTH: 1059
<212> TYPE: DNA
<213> ORGANISM: Artificial Sequence
<220> FEATURE:
<223> OTHER INFORMATION: Fusion protein

<400> SEQUENCE: 36

```
atgggcagca gccatcatca tcatcatcac agcagcggcc tggtgccgcg cggcagccat      60
atggctagcg agaaagaagc actgaagaaa ataatagaag accaacaaga atccctaaac     120
aaaactagca tgactggtgg acagcaaatg ggtcgggatc cgaattcgag ctccgtcgac     180
aagcttgcgg ccgcactcga gaaagaagca ctgaagaaaa taatagaaga ccaacaagaa     240
tccctaaaca aaactaggga cgtcatggtg agcaagggcg aggagctgtt caccggggtg     300
gtgcccatcc tggtcgagct ggacggcgac gtaaacggcc acaagttcag cgtgtccggc     360
gagggcgagg gcgatgccac ctacggcaag ctgaccctga agttcatctg caccaccggc     420
aagctgcccg tgccctggcc caccctcgtg accaccctga cctacggcgt gcagtgcttc     480
agccgctacc ccgaccacat gaagcagcac gacttcttca gtccgccat gcccgaaggc      540
tacgtccagg agcgcaccat cttcttcaag gacgacggca actacaagac ccgcgccgag     600
gtgaagttcg agggcgacac cctggtgaac cgcatcgagc tgaagggcat cgacttcaag     660
gaggacggca acatcctggg gcacaagctg gagtacaact acaacagcca caacgtctat     720
atcatggccg acaagcagaa gaacggcatc aaggtgaact tcaagatccg ccacaacatc     780
gaggacggca gcgtgcagct cgccgaccac taccagcaga cacccccat cggcgacggc       840
cccgtgctgc tgcccgacaa ccactacctg agcacccagt ccgccctgag caaagacccc     900
aacgagaagc gcgatcacat ggtcctgctg gagttcgtga ccgccgccgg gatcactctc     960
ggcatggacg tcagtactga gaaggaagca ctgaagaaaa taatagaaga ccaacaagaa    1020
tccctaaaca aaactagtca ccaccaccac caccactga                           1059
```

<210> SEQ ID NO 37
<211> LENGTH: 352
<212> TYPE: PRT
<213> ORGANISM: Artificial Sequence
<220> FEATURE:
<223> OTHER INFORMATION: Fusion protein

<400> SEQUENCE: 37

Met Gly Ser Ser His His His His His His Ser Ser Gly Leu Val Pro
1               5                   10                  15

Arg Gly Ser His Met Ala Ser Glu Lys Glu Ala Leu Lys Lys Ile Ile
            20                  25                  30

-continued

Glu Asp Gln Gln Glu Ser Leu Asn Lys Thr Ser Met Thr Gly Gly Gln
            35                  40                  45

Gln Met Gly Arg Asp Pro Asn Ser Ser Val Asp Lys Leu Ala Ala
 50                  55                  60

Ala Leu Glu Lys Glu Ala Leu Lys Lys Ile Ile Glu Asp Gln Gln Glu
 65                  70                  75                  80

Ser Leu Asn Lys Thr Arg Asp Val Met Val Ser Lys Gly Glu Leu
                85                  90                  95

Phe Thr Gly Val Val Pro Ile Leu Val Glu Leu Asp Gly Asp Val Asn
                100                 105                 110

Gly His Lys Phe Ser Val Ser Gly Glu Gly Glu Gly Asp Ala Thr Tyr
            115                 120                 125

Gly Lys Leu Thr Leu Lys Phe Ile Cys Thr Thr Gly Lys Leu Pro Val
 130                 135                 140

Pro Trp Pro Thr Leu Val Thr Thr Leu Thr Tyr Gly Val Gln Cys Phe
145                 150                 155                 160

Ser Arg Tyr Pro Asp His Met Lys Gln His Asp Phe Phe Lys Ser Ala
                165                 170                 175

Met Pro Glu Gly Tyr Val Gln Glu Arg Thr Ile Phe Phe Lys Asp Asp
                180                 185                 190

Gly Asn Tyr Lys Thr Arg Ala Glu Val Lys Phe Glu Gly Asp Thr Leu
            195                 200                 205

Val Asn Arg Ile Glu Leu Lys Gly Ile Asp Phe Lys Glu Asp Gly Asn
 210                 215                 220

Ile Leu Gly His Lys Leu Glu Tyr Asn Tyr Asn Ser His Asn Val Tyr
225                 230                 235                 240

Ile Met Ala Asp Lys Gln Lys Asn Gly Ile Lys Val Asn Phe Lys Ile
                245                 250                 255

Arg His Asn Ile Glu Asp Gly Ser Val Gln Leu Ala Asp His Tyr Gln
                260                 265                 270

Gln Asn Thr Pro Ile Gly Asp Gly Pro Val Leu Leu Pro Asp Asn His
            275                 280                 285

Tyr Leu Ser Thr Gln Ser Ala Leu Ser Lys Asp Pro Asn Glu Lys Arg
 290                 295                 300

Asp His Met Val Leu Leu Glu Phe Val Thr Ala Ala Gly Ile Thr Leu
305                 310                 315                 320

Gly Met Asp Val Ser Thr Glu Lys Glu Ala Leu Lys Lys Ile Ile Glu
                325                 330                 335

Asp Gln Gln Glu Ser Leu Asn Lys Thr Ser His His His His His
            340                 345                 350

<210> SEQ ID NO 38
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(17)
<223> OTHER INFORMATION: n is a, c, g, or t

<400> SEQUENCE: 38
tttttggatc csargtnmag ctgsagsagt cwgg        34

<210> SEQ ID NO 39

```
<211> LENGTH: 30
<212> TYPE: DNA
<213> ORGANISM: Artificial Sequence
<220> FEATURE:
<223> OTHER INFORMATION: Primer

<400> SEQUENCE: 39
attgggacta gtttctgcga cagctggatt                                    30

<210> SEQ ID NO 40
<211> LENGTH: 32
<212> TYPE: DNA
<213> ORGANISM: Artificial Sequence
<220> FEATURE:
<223> OTHER INFORMATION: Primer

<400> SEQUENCE: 40
ggaagatctc ttgaccaggc atcctagagt ca                                 32

<210> SEQ ID NO 41
<211> LENGTH: 36
<212> TYPE: DNA
<213> ORGANISM: Artificial Sequence
<220> FEATURE:
<223> OTHER INFORMATION: Primer

<400> SEQUENCE: 41
tttttgaatt ctgayattgt gmtsacmcar wctmca                             36

<210> SEQ ID NO 42
<211> LENGTH: 32
<212> TYPE: DNA
<213> ORGANISM: Artificial Sequence
<220> FEATURE:
<223> OTHER INFORMATION: Primer

<400> SEQUENCE: 42
tttttgggcc cggatacagt tggtgcagca tc                                 32

<210> SEQ ID NO 43
<211> LENGTH: 40
<212> TYPE: DNA
<213> ORGANISM: Artificial Sequence
<220> FEATURE:
<223> OTHER INFORMATION: Primer

<400> SEQUENCE: 43
ccatggcgga ctacaaagat attgtgctga cccagtctcc                         40

<210> SEQ ID NO 44
<211> LENGTH: 53
<212> TYPE: DNA
<213> ORGANISM: Artificial Sequence
<220> FEATURE:
<223> OTHER INFORMATION: Primer

<400> SEQUENCE: 44
ccagaaccac caccaccaga accaccacca ccggatacag ttggtgcagc atc          53

<210> SEQ ID NO 45
<211> LENGTH: 58
<212> TYPE: DNA
<213> ORGANISM: Artificial Sequence
<220> FEATURE:
<223> OTHER INFORMATION: Primer

<400> SEQUENCE: 45
```
tggtggttct ggcggcggcg gctccggtgg tggtggatcc gaagttaagc tggaggag        58

<210> SEQ ID NO 46
<211> LENGTH: 28
<212> TYPE: DNA
<213> ORGANISM: Artificial Sequence
<220> FEATURE:
<223> OTHER INFORMATION: Primer

<400> SEQUENCE: 46
gcggccgcga catttgggaa ggactgac        28

<210> SEQ ID NO 47
<211> LENGTH: 52
<212> TYPE: DNA
<213> ORGANISM: Artificial Sequence
<220> FEATURE:
<223> OTHER INFORMATION: Primer

<400> SEQUENCE: 47
cggcccagcc ggccatggcg gactacaaag aagttaagct gcaggagtca gg        52

<210> SEQ ID NO 48
<211> LENGTH: 50
<212> TYPE: DNA
<213> ORGANISM: Artificial Sequence
<220> FEATURE:
<223> OTHER INFORMATION: Primer

<400> SEQUENCE: 48
gagccgccgc cgccagaacc accaccacca gagacagtga ccagagtccc        50

<210> SEQ ID NO 49
<211> LENGTH: 53
<212> TYPE: DNA
<213> ORGANISM: Artificial Sequence
<220> FEATURE:
<223> OTHER INFORMATION: Primer

<400> SEQUENCE: 49
ggcggcggcg gctccggtgg tggtggatcc gacattgtga tcacacagtc tcc        53

<210> SEQ ID NO 50
<211> LENGTH: 29
<212> TYPE: DNA
<213> ORGANISM: Artificial Sequence
<220> FEATURE:
<223> OTHER INFORMATION: Primer

<400> SEQUENCE: 50
gcggccgcgg atacagttgg tgcagcatc        29

<210> SEQ ID NO 51
<211> LENGTH: 66
<212> TYPE: DNA
<213> ORGANISM: Artificial Sequence
<220> FEATURE:
<223> OTHER INFORMATION: Primer

<400> SEQUENCE: 51
ggcgccggcg gctccggtgg tggtggttcc ggtggtggtg gctccatggc ggactacaaa        60
gaggtc        66

<210> SEQ ID NO 52

-continued

```
<211> LENGTH: 41
<212> TYPE: DNA
<213> ORGANISM: Artificial Sequence
<220> FEATURE:
<223> OTHER INFORMATION: Primer

<400> SEQUENCE: 52
ggatccacca ccaccagaga cagtgaccag agtcccttgg c                    41

<210> SEQ ID NO 53
<211> LENGTH: 28
<212> TYPE: DNA
<213> ORGANISM: Artificial Sequence
<220> FEATURE:
<223> OTHER INFORMATION: Primer

<400> SEQUENCE: 53
ggatccgaca ttgtgctcac acagtctc                                   28

<210> SEQ ID NO 54
<211> LENGTH: 66
<212> TYPE: DNA
<213> ORGANISM: Artificial Sequence
<220> FEATURE:
<223> OTHER INFORMATION: Primer

<400> SEQUENCE: 54
ggcgccagaa ccaccaccac cagaaccacc accaccgggc ccggatacag ttggtgcagc  60
atcagc                                                           66

<210> SEQ ID NO 55
<211> LENGTH: 20
<212> TYPE: PRT
<213> ORGANISM: Clostridium tetani

<400> SEQUENCE: 55

Asn Tyr Ser Leu Asp Lys Ile Ile Val Asp Tyr Asn Leu Gln Ser Lys
1               5                   10                  15

Ile Thr Leu Pro
            20
```

US 9,487,585 B2

ANTIBODIES AGAINST 6-SULFO-LACNAC-POSITIVE HUMAN DENDRITIC CELLS, AND THEIR USE

BACKGROUND OF THE INVENTION

The invention concerns a composition which contains antibodies against human dendritic cells whose surface has the P-selectin glycoprotein ligand 1 (PSGL-1) with the O-bound glycan structure 6-sulfo N-acetyl lactosamine (6-sulfo LacNAc) 6-sulfo LacNAc (herein also referred to as "slan-DC") and which can influence the immune response via slan-DCs. Furthermore, the invention concerns the diagnostic and therapeutic use of the composition according to the invention. The composition according to the invention is suited for the use in the field of medicine, pharmacy and in biomedical research.

Faulty regulations of the immune system can lead to serious illnesses which are characterized either by immune deficiency or by excessive immunological reactions against essentially harmless antigens or even the body's own antigens. Serious infections or tumor illnesses are directly linked to an inadequate immune response.

The mechanism of the origin of these illnesses is still not yet elucidated completely; this complicates the development of causal therapies against the named illnesses. It is known that dendritic cells (DCs) are capable of, as a function of the signals which they receive, either activating the immune system or inactivating it. The inactivation of the immune system is also called a state of tolerance which exists relative to a discrete antigen.

DCs are capable of activating the immune system antigen-specifically, i.e., to mediate an immunological reaction against a specific antigen, in that the antigen is presented by activated DCs. When a specific antigen is presented by non-activated DCs, an immunological reaction is prevented against the antigen and even tolerance is induced against the antigen (Janeway, Immunologie (7th edition 2009); chapter 7.26, page 385).

In this way, it is in principle possible to therapeutically treat the aforementioned illnesses by specifically influencing the signals transmitted by the DCs. It is problematic in this context that DCs are not of a uniform cell population and different subpopulations of the DCs are suited differently well to cause a relief of the clinical picture via therapeutically given substances which influence the signals of the DCs. This requires systems which bind specifically and with high affinity to dendritic cells but not to other cells.

WO 2009/061966 discloses an antibody which is also referred to as DEC-205 and which specifically binds human DCs and epithelial cells.

EP 1 078 060 B1 discloses antibodies which are directed against DCs. One of the disclosed antibodies is the monoclonal IgM antibody "M-DC8" which binds specifically to a defined subpopulation of the DCs. On account of the specific bond of the antibody M-DC8 to this subpopulation of the DCs, they were initially named "M-DC8 DC" (Schakel et al., European J. Immunol., 1998, 28, 4084-93). It was later found that this subpopulation is characterized in that on the surface of the DC the P-selectin glycoprotein ligand 1 (PSGL-1) comprises the O-bound glycan structure 6-sulfo N-acetyl lactosamine (6-sulfo LacNAc, "slan") (Schäkel et al., Immunity, 2002, 17, 289-301; Wehner et al., Int J Cancer. 2009, 15, 358-66). Hence, this subpopulation of the DCs was called from this time on "slan-DC" (Schäkel et al., Immunity, 2006, 24, 767-77). It was found that this subpopulation is particularly suitable for influencing the immune system.

A further monoclonal IgM antibody is known which binds specifically to slan-DC and also is referred to as DD2 (Schäkel et al., Immunity, 2002, 17, 289-301).

Handling is a problem for a therapeutic use of IgM antibodies in monoclonal form. IgM antibodies cannot be separated with certainty from small virus particles because of their high molecular weight. Their bad solubility complicates their purification, storage and application as a medicament. Only IgM antibodies in the form of antibody fragments can be used, in particular single chain antibodies, which exhibit a satisfactory binding affinity of a single monomer.

EP 1 078 060 B1 discloses furthermore the therapeutic use of the antibodies which are directed against DCs for targeting target cells. In this context, a recruitment of the target cells to the DCs is enabled by bispecific antibodies which are directed against a surface antigen on DCs and against a surface antigen on target cells, respectively. In particular tumor cells are to be bound to DCs by this implementation in order to cause the admission of the tumor cell. Antigen epitopes of the tumor cells or in general of the target cells are presented on the surface of the DIXs in this way and are intended to cause a specific immune response against the target cells. It is critical in this context that for triggering this immune response against the target cells an additional stimulus is necessary which leads to the activation of the DCs. With the currently known methods in which a stimulus (herein also "co-stimulus" because it is applied always in combination with the antibody) is administered separately and binds e.g. on pattern recognition receptors (PRR) on DCs and thereby activates the DCs, no specific transport of this stimulus to DCs can be generated. A large amount of this stimulus must therefore be administered systemically in order to achieve an effect. This systemic administration has the disadvantage that thereby DCs are not exclusively influenced but also other cells of the immune system may be affected and activated by the stimuli; this leads to undesirable side reactions. When, on the other hand, too little stimulus is administered, DCs are not activated enough and cannot provide the desired effect but cause even the opposite effect, induce an induction of peripheral tolerance.

To mediate tolerance via DCs, the DCs must be present in the inactivated state; a concurrent administration of a co-stimulus is not carried out. In this context, on account of the huge number of possible antigens, it is of great importance to provide therapy systems that enable the targeted transport of different antigens to DCs with low production expenditure.

Object of the invention is to provide a therapy system that is suitable for transporting co-stimuli that activate DCs together with the antigen in a targeted fashion to slan-DCs and that enable with low production expenditure the targeted transport of numerous different antigens to slan-DCs. Furthermore, it is an object of the invention to provide antibodies which are suitable for the use in such therapy systems.

SUMMARY OF THE INVENTION

The object is solved according to the invention by a composition which comprises the following components:
  a) at least one antibody which binds specifically to human dendritic cells whose surface has the P-selectin glycoprotein ligand 1 (PSGL-1) with the O-bound glycan structure 6-sulfo N-acetyl lactosamine (6-sulfo LacNAc) (these antibodies are referred to herein also as "anti-slan antibodies"), b) at least one an binding unit, which to a co-stimulus, which binds to a receptor specific for the co-stimulus on dendritic cells and thereby causes the modulation, preferably the activation, of aforesaid dendritic cells, and c) at least one antigen.

The invention is based on the idea that co-stimuli can be transported in a target fashion to dendritic cells (DCs) in that they are bound to a transport structure containing an anti-slan antibody and a binding unit which binds the co-stimulus directly. Co-stimuli or stimuli are suitable for causing the modulation, in particular the activation of dendritic cells. Co-stimuli which cause the activation of dendritic cells are referred to herein also as "activating co-stimuli". For this purpose, the co-stimulus (for example, activating TLR ligands like nucleic acids) binds to a receptor of the dendritic cells that is specific for the co-stimulus (for example, Toll-like receptors) and, by the binding action, a signal chain is triggered which modulates the further development of the DCs. In this context, inhibiting co-stimuli cause the DC not to be activated. Activating co-stimuli cause the DCs to be activated. The co-stimulus is thus a ligand which binds to a special receptor of the DCs. Accordingly, the terms "stimulus", "co-stimulus", and "ligand effecting the modulation of dendritic cells" are used synonymously. Furthermore, the terms "activating stimulus", "activating co-stimulus", and "ligand effecting the activation of dendritic cells" are used synonymously. The antigen against which the immune response is to be influenced is transported also at the same time with the transport structure. When the dendritic cell is activated after antigen transport, an immunological reaction is triggered which is directed against the antigen. When the dendritic cell is not activated after antigen transport, tolerance is imparted against the antigen and no pathogenic immune response is induced against the antigen.

The composition according to the invention comprises for this purpose at least one anti-slan antibody which serves for binding to human slan-DCs, at least one, preferably several, in particular 1 to 5, preferably 3 to 5, binding units which bind the co-stimulus (preferably an activating co-stimulus) (they are referred to herein also as "binding unit binding to a ligand" or more simply as "binding unit"), and the antigen to be transported. In this context, three minimum components are connected with each other in this context so that they form preferably a complex and are not present as separate single components. Only by this stable compound it is made sure that all components are transported at the same time to the slan-DCs. In this context, the compound of the three components can be designed in different ways, preferably they are present in a fusion protein or in several fusion proteins which are connected to each other by specific or covalent bonds.

The "anti-slan antibody" is to be understood in the context of the invention as an antibody which binds specifically to the surface of slan-DCs. The term "antibody" is understood in the context of the invention as comprising all antibodies, antibody fragments and derivatives thereof which are capable of binding specifically to an antigen. Antibodies include the complete monoclonal antibodies and also the epitope binding fragments of these antibodies. In this context, the epitope binding fragments (here also referred to as antibody fragments or antibody derivatives) comprise all parts of the antibody which are able to bind to the antigen. Antibody fragments in the context of the invention contain, but are expressly not limited to, Fab, Fab', F(ab')$_2$, Fd, single chain (single chain) variable fragments (scFv), single chain antibodies, disulfide linked variable fragments (sdFv) and fragments that contain either a variable region of the light chain ($V_L$) or a variable region of the heavy chain ($V_H$). Also included are recombinant antibodies, like diabodies, triabodies and tetrabodies. Antibody fragments contain the variable regions either alone or in combination with other regions which are selected from the hinge region, and the first, second and third segment of the constant region ($C_H1$, $C_H2$, $C_H3$). Also comprised by the term "antibody" are chimeric antibodies in which different parts of the antibody originate from different species, as for example antibodies with a murine variable region which is combined with a human constant region.

Also comprised by the term "antibody" are humanized antibodies. The aim of humanization of antibodies resides in the reduction of the immunogenicity of a xenogenic antibody, as for example murine antibodies, for use in the human system, wherein the full binding affinity and the antigen specificity is preserved. Humanized antibodies can be produced in different ways, for example, by resurfacing and CDR grafting. In resurfacing, all non-CDR regions on the surface of the antibody are changed by a combination of molecular modeling, statistical analyses and mutagenesis so that they resemble the surface of antibodies of the target organism. In CDR grafting, the CDR regions according to the invention are introduced into human variable regions.

Antibody fragments are linked together optionally by a linker. The linker comprises a short (preferably a length of 10 to 50 amino acid residues) flexible peptide sequence which is so selected that the antibody fragment has such a three-dimensional folding of the $V_L$ and $V_H$ that it exhibits the antigen specificity of the complete antibody.

The term "variable region" is defined according to the invention as the parts of the heavy and light chains of the antibodies which differ in their sequence between antibodies and determine the specificity of the antibody and binding to its antigen. The variability is not distributed evenly in the variable region in this context. It is usually concentrated within three defined segments of the variable region which are referred to complementarity determining regions (CDRs) or also hypervariable regions and exist in the variable regions of the light as well as the heavy chains. The more strongly preserved parts of the variable regions are called frame regions (framework regions). The variable regions of the heavy and light chains contain four framework regions which predominantly have a beta sheet structure, wherein every framework region is connected with three CDRs which form loops which connect the beta sheet structures and in some cases form a part of the beta sheet structure. The CDRs of the respective chain are brought by the framework regions into immediate proximity and contribute together with the CDRs of the other chain to the formation of the antigen binding region of the antibodies. Preferably, the anti-slan antibodies comprise at least one variable region of the heavy chain ($V_H$) and a variable region of the light chain ($V_L$) in form of an scFv.

In the context of the invention, the term specific binding of an antibody to a specific antigen is to be understood such that an antibody with a high affinity binds to the specific antigen and binds with a clearly lower affinity and preferably does not bind to other antigens.

Preferred anti-slan antibodies comprise the structures, optionally humanized, listed in Table 1:

TABLE 1

| | Amino acid sequence of the variable region of the heavy chain | Amino acid sequence of the variable region of the light chain |
|---|---|---|
| DD2 | SEQ ID No. 19 | SEQ ID No. 20 |
| M-DC8 | SEQ ID No. 21 | SEQ ID No. 22 |
| MB4 | SEQ ID No. 12 | SEQ ID No. 14 |
| MB6 | SEQ ID No. 16 | SEQ ID No. 18 |

The binding unit which binds the co-stimulus is so configured that it binds specifically to the co-stimulus. The term "binding unit" in the context of the invention means any molecular structure which binds defined substances specifically. In this context, depending on the selection of the co-stimulus to be bound the binding unit comprises different structures. When the co-stimulus is a nucleic acid, the binding unit is so configured that it is suitable for binding nucleic acids. When the co-stimulus is a bacterial glycan structure, the binding unit is so configured that it is suitable for binding bacterial glycan structures.

Preferably, the binding unit is connected with the anti-slan antibody and/or with the antigen by a covalent bond. The covalent bond is preferably a peptide bond.

Preferably, a composition according to the invention contains a binding unit which binds an activating co-stimulus. Co-stimuli which are suitable for the activation of DCs are known in the prior art and comprise in particular ligands which bind to so-called pattern recognition receptors (PRRs). Preferably, the co-stimulus is a ligand of C-type lectin receptors or particularly preferred Toll-like receptors. It is basically unimportant whether the receptors upon whose binding the activating signals are being triggered are located on the cell surface of the DCs or are intracellularly located. After binding of the transport structure to the slan-DC by the anti-slan antibody, the co-stimulus binds to its respective receptor either before or after the internalization of the transport structure.

Preferably, a composition according to the invention contains a binding unit which is suitable for binding nucleic acids. Accordingly, co-stimuli in the form of nucleic acids can be transported. In particular TLR ligands can be transported therewith, preferably ssRNA as a ligand of TLR7 or TLR8 or unmethylated bacterial DNA (CpG DNA) as a ligand of TLR9.

Preferably, the binding unit is a peptide. The amino acid sequence comprises preferably 10-50 amino acids. Preferably, the peptide has the structure of an alpha-helix. In this context, preferably the linker peptide comprises an amino acid sequence according to SEQ ID No. 23, in particular an amino acid sequence according to SEQ ID No. 24, or an amino acid sequence with an amino acid sequence identity of at least 90%, preferably at least 95%, to the aforementioned sequences. Peptides of this structure are suitable for binding nucleic acids.

Preferably, in the compositions according to the invention a peptide with an alpha helix structure is contained as a binding unit which is suitable for binding nucleic acids.

The antigen which is contained in a composition according to the invention is preferably a peptide or protein. In this context, the antigens are contained in complete form or as fragments in the composition according to the invention. Preferred antigens are tumor antigens, bacterial antigens, auto-antigens or allergens. Particularly preferred antigens are tumor antigens, i.e., antigens which are produced by cancer cells and which are present, in particular on the surface of tumor cells. Of these, tumor antigens selected from HERs/neu, EGFR, VEGF, CAMPATH 1-antigen, CD22, CD33, CEA, prostate stem cell antigen (PSCA), CA-125, HLA-DR, mucin-1, survivin, alpha-1-fetoprotein, tyrosinase are preferred. Further preferred tumor antigens are antigens which are not produced selectively by cancer cells but are present in tumors in high concentrations. Of these, human nuclear antigens, in particular human La protein, are particularly preferred.

Further preferred antigens are allergens, i.e., essentially innocuous substances for the human body, which trigger an oversensitivity reaction of the immune system. All allergens are suitable basically in the composition according to the invention which are suited for combination with the anti-slan antibody and the binding unit. Proteins or peptides are particularly preferred as allergens.

Preferably, the anti-slan antibody and the binding unit are present as a fusion protein or the antigen and the binding unit are present as a fusion protein.

For producing recombinant fusion proteins (for simplification referred to herein also as fusion proteins), a fusion gene is generated in that a gene sequence is fused after removal of a stop codon with another gene sequence. Upon translation of this fusion gene a fusion protein is generated. Fusion proteins comprise a protein domain which is merged with another domain. In this context, at least one peptide domain (as a linker peptide) is contained, optionally other protein domains are contained. The functionality of the individual protein domains is preserved in fusion proteins because the functional domains of proteins mostly have a modular configuration so that the amino acid sequence of a protein domain which has assigned a certain function can be separated from the rest of the protein without its functionality being affected.

Particularly preferred, the anti-slan antibody, the binding unit, and the antigen in the composition according to the invention are present as a fusion protein. In this context, preferably the binding unit is a preferably alpha-helical peptide which is linked by peptide bonds with the anti-slan antibody and the antigen. Preferably, in this context the binding unit fulfills at the same time the function of a linker peptide. In this context, preferably the linker peptide comprises an amino acid sequence according to SEQ ID No. 23, in particular an amino acid sequence according to SEQ ID No. 24, or an amino acid sequence with an amino acid sequence identity of at least 90%, preferably at least 95%, relative to the aforementioned sequences. To cause in this case an effective targeting of these fusion proteins to slan DCs, an especially high binding affinity to slan-DCs is necessary. Hence, in this embodiment especially anti-slan antibodies, optionally humanized, are suitable which comprise the CDR regions of the antibodies MB4 or MB6 according to the invention.

Compositions according to the invention contain preferably no other substances which specifically bind immunophenotype surface features of target cells in addition to the anti-slan antibodies. In particular fusion proteins according to the invention contain no antibodies which specifically bind to surface features, in particular protein and glycan structures, of other cells of the immune system, except DC, and also no ligands which specifically bind to surface features, in particular receptors, of cells of the immune system, except DC. The components of the composition are transported therefore selectively to slan-DCs. Compositions according to the invention do not have the function of recruiting other effector cells, like in particular T cells, directly to DCs. Hence, in particular no antibodies or ligands are contained in the compositions according to the invention which bind to surface features of T cells.

Preferably, the composition according to the invention contains, in addition to the aforementioned components a), b) and c), at least a binding unit (herein "further binding unit") which binds specifically at least one of the components a), b) or c) of the compositions according to the invention. In case that the further binding unit binds to the anti-slan antibody or the binding unit, binding occurs in such a way that the functionality of antibody or binding unit is not affected. This means that the anti-slan antibody binds after binding with the same affinity to slan-DCs or that the binding unit binds with the same affinity to the co-stimulus.

The further binding unit is thus configured such that it is suitable for binding to the anti-slan antibody, to the binding unit that binds a ligand, or to the antigen. Preferably, the further binding unit is an antibody. This antibody does not bind to slan-DCs.

Preferably, the further binding unit is suitable for binding to a binding unit that binds a ligand.

Particularly preferred compositions according to the invention are characterized in that the binding unit is a peptide and the further binding unit is an antibody which binds the peptide specifically. Of these, further preferred peptides comprise the following amino acid sequence: EKEALKKIIEDQQESLNK (SEQ ID No. 23, corresponds to amino acids No. 311-No. 328 of the human La protein according to SEQ ID No. 25). These peptides are referred to herein also as "E7B6". In combination with these peptides, the further binding unit is preferably an antibody (herein also referred to as "7B6") which comprises the following CDR regions and specifically binds the peptide with SEQ ID No. 23:
  a) variable region of the heavy chain ($V_H$): CDR1 SEQ ID No. 26, CDR2 SEQ ID No. 27, CDR3 SEQ ID No. 28, and
  b) variable region of the light chain ($V_L$): CDR1 SEQ ID No. 29, CDR2 SEQ ID No. 30, CDR3 SEQ ID No. 31.

The further binding unit is connected preferably with the anti-slan antibody and/or with the antigen by a covalent bond. The covalent bond is preferably a peptide bond. Preferably, an antibody is contained as a further binding unit in a composition according to the invention.

Preferably, at least two fusion proteins are contained in compositions according to the invention wherein one of them contains the antigen and the other the anti-slan antibody. Both fusion proteins are so configured that they form a complex with each other, i.e. in each case a domain of one fusion protein engages by a specific binding action a domain of the further fusion protein. This bond is preferably an antibody antigen bond. In this configuration, the fusion protein which contains the anti-slan antibody serves for binding to slan-DC. Since the complex contains the further fusion protein with the antigen, the antigen is transported specifically to slan-DCs. This configuration of a complex of at least two fusion proteins which bind each other specifically is referred to herein also as "modular construction". In this way, advantageously with one fusion protein which contains the anti-slan antibody any number of fusion proteins which contain antigens can be combined.

Compositions according to the invention are preferred in which either
  a) the anti-slan antibody and the binding unit are present as a fusion protein and the further binding unit and the antigen are present as fusion protein, or
  b) the anti-slan antibody and the further binding unit are present as a fusion protein and the antigen and the binding unit are present as a fusion protein.

Since the binding unit and the further binding unit are present in different fusion proteins and bind each other specifically, both fusion proteins are present in the composition according to the invention as a complex.

In a preferred embodiment of the invention according to a), the composition according to the invention contains the anti-slan antibody and, as a binding unit, a peptide in the form of a fusion protein. Furthermore, the composition according to the invention contains in this case a fusion protein which contains the antigen and an antibody which binds the peptide specifically. The peptide has preferably an alpha-helix structure. In particular the peptide comprises an alpha helical structure that is characterized by the amino acid sequence according to SEQ ID No. 23, in particular by the amino acid sequence according to SEQ ID No. 24, or by amino acid sequences with an amino acid sequence identity of at least 90%, preferably at least 95%, relative to the aforementioned sequences. Particularly preferred in this embodiment is the combination of a peptide E7B6 as a binding unit with an antibody 7B6 as a further binding unit. In these compositions according to the invention, the structures listed in Table 1 that are optionally humanized are preferred as anti-slan antibodies, and in particular the structures of the antibodies MB4 or MB6.

In a preferred embodiment of the invention according to b), the composition according to the invention contains the anti-slan antibody and as a further binding unit an antibody (herein also "further antibody") wherein the anti-slan antibody and the further antibody are present in the form of a bispecific antibody. Preferably, the antibodies are present in the form of a single chain bispecific diabody (scBsDb) or single chain bispecific tandem antibody (scBsTaFv). The further antibody is not identical with the anti-slan antibody and does not bind to slan-DCs. Preferably, the further antibody binds specifically to a structural domain of the further fusion protein of the composition according to the invention which contains the antigen. When combining the bispecific antibody of anti-slan antibodies and further antibody with the further fusion protein containing the antigen, a complex is then formed.

In this context, the avidity of the anti-slan antibodies is increased when the further fusion protein contains several structural domains which the further antibody binds. This leads to binding of large complexes with several bispecific antibodies and to an improved binding to slan-DCs. The structural domain which the further antibody binds is preferably an alpha-helix structure which is present preferably in the form of a linker peptide in the further fusion protein. Preferably, the further fusion protein comprises several of these linker peptides, preferably more than 2, further preferred 2 or 3.

Particularly preferred, the further antibody of the fusion protein according to the invention binds an alpha helical peptide sequence that is characterized by the amino acid sequence according to SEQ ID No. 23, in particular by the amino acid sequence according to SEQ ID No. 24, or by amino acid sequences with an amino acid sequence identity of at least 90%, preferably at least 95%, relative to the aforementioned sequences. Particularly preferred in this embodiment is the combination of a peptide E7B6 as a binding unit with an antibody 7B6 as a further binding unit. In these compositions according to the invention, the structures listed in Table 1, optionally humanized, are preferred as anti-slan antibodies, in particular the structures of the antibodies MB4 or MB6.

The compositions according to the invention are suited for a therapeutic use, in particular in a human being. In this context, the compositions can be used for therapies in which tolerance is to be induced against an antigen as well as for therapies in which an immune response is to be induced against an antigen.

For therapeutic uses, it is desirable when the antibodies transport as effectively as possible the antigen to the slan-DCs. Antibodies with a high binding affinity are suited especially advantageously for binding to slan-DCs. Particularly preferred, the anti-slan antibodies comprise regions determining complementarity (complementarity determining regions, CDRs) which comprise the following amino acid sequences:

a) variable region of the heavy chain ($V_H$):

```
                                        (SEQ ID No. 1)
    CDR1 TYGVH, (SEQ ID No. 2)
    CDR2 VIWSGGGTDFNVAFXS, wherein X is selected from M, I, F or I,
    preferably from M or I, (SEQ ID No. 5)
    CDR3 RTTNDGNYAFAY
    and
``` b) variable region of the light chain ($V_L$):

```
                                        (SEQ ID No. 6)
CDR1 RSSQNILHSDGXTYLE, wherein X is selected from S, T, N, Q, H, K or R,
preferably from S or N, (SEQ ID No. 9)
CDR2 KVSNRFS
and (SEQ ID No. 10)
CDR3 FQGSHVPWT.
```

Furthermore, the invention comprises antibodies which comprise the aforementioned CDR regions in this combination. The antibodies according to the invention are preferably present as monoclonal antibodies, as antibody fragments, or in the form of fusion proteins, in particular as bispecific antibodies. Monovalent antibodies in the form of scFv fragments, F(ab')$_2$, are preferred. Further preferred are bispecific antibodies in the form of single chain bispecific diabodies (scBsDb) or single chain bispecific tandem antibodies (scBsTaFv). Advantageously, anti-slan antibodies according to the invention bind in the form of scFv fragments with a clearly higher affinity to slan-DCs than antibodies which are known in the prior art.

The antibodies according to the invention with the aforementioned CDR regions according to SEQ ID Nos. 1, 2, 5, 6, 9 and 10 bind specifically to human dendritic cells whose surface has the P-selectin glycoprotein ligand 1 (PSGL-1) with the O-bound glycan structure 6-sulfo N-acetyl lactosamine (6-sulfo LacNAc). Antibodies according to the invention are therefore anti-slan antibodies.

Antibodies according to the invention are preferred, in which the CDR2 of the variable region of the heavy chain comprises the amino acid sequence according to SEQ ID No. 3 and CDR1 of the variable region of the light chain comprises the amino acid sequence according to SEQ ID No. 7 (these antibodies are referred to herein also as "MB4"). In this context, preferably the variable region of the heavy chain comprises the amino acid sequence according to SEQ ID No. 12 (corresponding nucleic acid sequence according to SEQ ID No. 11) and the variable region of the light chain comprises the amino acid sequence according to SEQ ID No. 14 (corresponding nucleic acid sequence according to SEQ ID No. 13), optionally in each case as a humanized structure.

Furthermore, antibodies are preferred in which the CDR2 of the variable region of the heavy chain comprises the amino acid sequence according to SEQ ID No. 4 and CDR1 of the variable region of the light chain comprises the amino acid sequence according to SEQ ID No. 8 (these antibodies are referred to herein also as "MB6"). In this context, preferably the variable region of the heavy chain comprises the amino acid sequence according to SEQ ID No. 16 (corresponding nucleic acid sequence according to SEQ ID No. 15) and the variable region of the light chain comprises the amino acid sequence according to SEQ ID No. 18 (corresponding nucleic acid sequence according to SEQ ID No. 17), optionally in each case as a humanized structure.

The antibodies were obtained by the immunization of mice with isolated human slan-DCs and subsequent hybridoma fusion (cf. embodiment 1).

The invention further comprises a nucleic acid sequence coding for an anti-slan antibody according to the invention.

The term "nucleic acids" in the context of the invention comprises, in addition to deoxyribonucleic acids (DNA) and ribonucleic acids (RNA), also all the other linear polymers in which the bases adenine (A), cytosine (C), guanine (G) and thymine (T) or uracil (U) are arranged in a suitable sequence (nucleic acid sequence). In this context, the invention also comprises the corresponding RNA sequences (in which thymine is replaced by uracil), complementary sequences and sequences with modified nucleic acid backbone or 3' terminus or 5' terminus. In this context, the term "nucleic acid sequences with modified backbone" comprises all the other linear polymers in which the bases adenine (A), cytosine (C), guanine (G) and thymine (T) or uracil (U) are arranged in a suitable sequence, as for example sequences with a phosphothioate, phosphoamidate or O-methyl derivatized backbone, peptide-nucleic acids (PNA) and locked nucleic acids (LNA) or mixed backbone. In this context, the term "modified 3' terminus or 5' terminus" comprises modifications which serve for stabilization as well as binding of markers. Examples of markers are enzymes, dyes or fluorescence dyes, radio nucleotides, as well as haptenes, as for example digoxigenin or biotin.

The nucleic acid sequence which codes for the antibody MB4 according to the invention preferably comprises the following nucleic acid sequences: variable region of the heavy chain SEQ ID No. 11 and variable region of the light chain SEQ ID No. 13. Preferably, the nucleic acid sequence which codes for the antibody MB6 according to the invention comprises the following nucleic acid sequences: variable region of the heavy chain SEQ ID No. 15 and variable region of the light chain SEQ ID No. 17.

Furthermore, the invention comprises an expression vector which contains a nucleic acid sequence according to the invention. In the context of the invention, an expression vector is to be understood as a plasmid, virus or other carrier containing a nucleic acid sequence according to the invention recombinantly by insertion or incorporation. The expression vector contains typically a replication start site, a promoter, as well as specific gene sequences which enable a phenotype selection of host cells that contain the expression vector.

Furthermore, the invention comprises a host cell or a non-human host organism which contain recombinantly a nucleic acid sequence according to the invention or an expression vector according to the invention.

A host cell is a naturally existing cell or a transformed or genetically modified cell line which contains at least one expression vector according to the invention. In this context, the invention comprises transient transfectants (e.g., by mRNA injection) or host cells in which at least one expression vector according to the invention is contained as a plasmid or artificial chromosome, as well as host cells in which an expression vector according to the invention is integrated stably into the genome of the host. The host cell is selected preferably from prokaryotes or eukaryotes. Preferred prokaryotes are selected from *Escherichia coli, Bacillus subtilis*. Preferred eukaryotes are yeast cells (e.g., *Saccharomyces cerevisiae, Pichia pastoris*), insect cells, amphibious cells or mammalian cells, as for example CHO, HeLa, HEK293.

Non-human host organisms contain an expression vector according to the invention which is integrated stably into the genome of the host organism or individual cells of the host organism. Preferred host organisms are plants, invertebrates or vertebrates, in particular Bovidae, *Drosophila melanogaster, Caenorhabditis elegans, Xenopus laevis*, Medaka, zebra fish or *Mus musculus*, or cells or embryos of the named organisms.

Furthermore, the invention comprises procedures for the production of an anti-slan antibody according to the invention, in which:
  a) a host cell according to the invention or a non-human host organism according to the invention is exposed to conditions under which an expression and optionally a secretion of the anti-slan antibody takes place and optionally
  b) the anti-slan antibody is at least partially purified.

Preferably, for this purpose, host cells according to the invention are grown (cultured) in a selective medium which selects for the growth of the cells which contain an expression vector according to the invention. The expression of the gene sequences of the expression vector results in the production of the anti-slan antibody according to the invention. The expressed anti-slan antibodies are then isolated and purified preferably by any conventional procedure, including extraction, precipitation, chromatography, electrophoresis or even by affinity chromatography.

Compositions according to the invention are suitable for therapeutic use in the treatment or prophylaxis of illnesses wherein either antigen-specifically an immune response is mediated or tolerance is induced. In this context, the respective antigens with the optionally necessary (preferably activating) co-stimulus are transported by the anti-sian antibodies or complexes formed therefrom to slan-DCs.

Illnesses in which antigen-specifically an immune response is to be triggered are in particular tumor illnesses or infections. In this context, compositions according to the invention are used for therapy in combination with a co-stimulus that activates the slan-DCs. Preferably, the activating co-stimulus is bound directly to a component of the composition according to the invention and is transported thus after administration in a targeted fashion to slan-DCs. Preferred activating co-stimuli are ligands of PRR, in particular of TLR. In particular, TLR ligands are used in combination with compositions according to the invention, preferably ssRNA as a ligand of TLR7 or TLR8, dsRNA as a ligand of TLR3, or unmethylated bacterial DNA (CpG DNA) as a ligand of TLR9.

The antigen contained in the composition is thereby transported directly to slan-DCs and is processed after binding of the anti-slan antibody to the cell surface by the slan-DCs and is presented on their surface. At the same time, the cell is activated by the co-stimulus. A pathogenic immunological reaction against the antigen is mediated by the antigen presentation of the activated slan-DCs. Antigens which are contained preferably in the composition according to the invention in this therapy variant are tumor antigens (for the treatment of tumor illnesses) or antigens of pathogens (for the treatment of infections). In this context, particularly preferred are the aforementioned tumor antigens.

The invention also comprises a pharmaceutical kit that a composition according to the invention and a ligand which causes the activation of human dendritic cells, in particular the activation of slan-DC, and binds to at least one component of the composition according to the invention, in association with a pharmaceutical suitable diluent or carrier.

The pharmaceutical kit preferably comprises in association with a pharmaceutical suitable diluent or carrier:
  a) a composition according to the invention comprising:
    a bispecific antibody, containing MB4 or MB6 as an anti-slan antibody and a 7B6 antibody,
    a fusion protein, containing a peptide according to SEQ U) No. 23 (E7B6) and a tumor antigen, and
  b) at least one TLR ligand selected from ssRNA and CpG DNA.

Preferably, the antibodies are present in the pharmaceutical kit according to the invention as chimeric or, particularly preferred, humanized antibodies which exhibit a reduced immunogenicity.

The pharmaceutical compositions according to the invention comprise different dosage forms. The pharmaceutical compositions are administered preferably parenterally, particularly preferred intravenously. In one embodiment of the invention, the parenteral pharmaceutical composition is present in an administration form which is suitable for injection. Particularly preferred pharmaceutical compositions are solutions, emulsions or suspensions of the antibody which is present in a pharmaceutically suitable diluent or carrier.

As carriers, water, buffered water, 0.4% saline solution. 0.3% glycine and similar solvents are preferably used. The solutions are sterile. The pharmaceutical compositions are sterilized by customary, well-known technologies. The compositions contain preferably pharmaceutically suitable excipients, as for example those that are required to obtain approximately physiological conditions and/or to increase the stability of the antibodies contained in the composition, as for example agents for adjusting the pH value and buffer agents, agents for adjusting the toxicity and the like, preferably selected from sodium acetate, sodium chloride, potassium chloride, calcium chloride and sodium lactate.

The pharmaceutical composition is preferably an injectable buffered solution which contains between 0.1 to 500 mg/ml of antibodies, particularly preferred between 0.1 to 250 mg/ml of antibodies, in particular together with 1 to 500 mmol/l of a buffer. The injectable solution can be present in a liquid as well as lyophilized dosage form. The buffer is selected preferably from histidine, sodium succinate, sodium citrate, sodium phosphate and potassium phosphate.

The invention also comprises the use of a pharmaceutical kit according to the invention or of a composition according to the invention for therapeutic treatment of tumor illnesses.

In this case, the antigen which is contained in the composition according to the invention is a tumor antigen. For therapeutic uses, a sterile composition according to the invention or a sterile pharmaceutical composition according to the invention which contains a pharmacological effective dosage amount of the antibodies is administered to a patient in order to treat tumor illnesses.

The illnesses in which antigen-specific tolerance is to be induced are in particular allergies, auto immune illnesses or transplant rejection reactions by a host versus graft reaction or prevention of a graft versus host reaction. In the therapeutic treatment of allergies, the antigens are allergens; in the therapeutic treatment of auto immune illnesses, the antigens are auto-antigens. In transplant rejection reactions, the antigens are in particular deviations in the "major" and "minor" histocompatibility antigens between donor and recipient. For the therapy of these illnesses, compositions according to the invention without additional co-stimulus are administered so that slan-DCs are not activated. In this way, the antigen contained in the composition according to the invention is processed by the slan-DCs and is presented on their surface. An inhibition of pathogenic immunological reactions on the antigen (tolerance induction against the antigen) is induced by the antigen presentation of non-activated slan-DCs and, in this way, the symptoms of the illness are alleviated.

Compositions according to the invention are suitable advantageously for the therapy of tumor illnesses. Since the ligands which can activate dendritic cells (DCs) can be transported in a targeted fashion to DCs, no systemic application of these ligands is necessary with compositions according to the invention. The ligands are transported especially to the DCs and can act only there. This prevents that other cells are activated and undesirable reactions triggered by these ligands which can usually bind also receptors on other cells, in particular on cells of the immune system. The antibodies according to the invention are suited especially advantageously for the use in compositions according to the invention because they exhibit, even in the form of scFv fragments, a higher binding affinity to slan-DCs than the known antibodies DD2 and M1DC-8.

Moreover, they are also superior to other known surface antigens on DCs which are used for targeting of DCs, in particular DEC-205. This is due to the fact that the slan-epitope is expressed selectively on slan-DCs while DEC-205 is expressed also on other tissues, e.g., epithelial cells in the thymus gland (Nonaka et al., J., Am. J Surg Pathol. 2007, 31:1038-44). In addition, the slan-epitope is already expressed on immature DCs, i.e., prior to uptake of antigen, while DEC-205 is down-regulated e.g. on Langerhans cells (immature DCs) in the skin and is up-regulated only after maturation (i.e., after uptake and activation by the antigen or co-factors) on the path to or in the lymph node (Ebner et al., Int. Immunol. 2004, 16, 877-87).

BRIEF DESCRIPTION OF THE DRAWINGS

With the aid of the following figures and embodiments the invention will be explained in more detail without limiting the invention thereto.

DESCRIPTION OF PREFERRED EMBODIMENTS

Embodiment 1

Providing Antibodies MB4 and MB6 According to the Invention

For generating and screening the respective hybridoma supernatents of the anti-slan antibodies MB4 and MB6, slan-DCs from freshly isolated peripheral blood lymphocyte preparation (PBMCs) were isolated by means of magnetic cell separation (MACS).

For the isolation of the slan-DCs, cell culture supernatent, containing the monoclonal IgM antibody M-DC8, was diluted in a ratio of 1:60 in PBS/2 mM EDTA. $10^9$ peripheral nucleus-containing cells each were incubated with 20 ml diluted cell culture hybridoma supernatent for 15 min. After incubation the cells are collected by centrifugation and are washed with 50 ml PBS/EDTA. The marked cells are isolated with anti-lgM magnetic beads of the company Miltenyi (Bergisch Gladbach). $10^9$ peripheral nucleus-containing cells each are re-suspended in 1 ml PBS/EDTA together with 120 μl anti-lgM beads and incubated for 15 min. Then the cells are washed with 50 ml PBS/ETDA. $10^9$ cells each were re-suspended before separation by MACS in 5 ml PBS/EDTA.

Slan-DCs isolated in this way were used for immunization of mice. Per immunization and per mouse $5 \times 10^5$ to $1 \times 10^6$ cells were applied intravenously. The mice were immunized before the hybridoma fusion at least four times. For the hybridoma fusion, spleen cells of the immunized mice were fused with myeloma cells (P3xAg 8.653; ATCC CRL, 1580) in a ratio of 1:1 to 10:1 by drop-wise addition of polyethylene glycol. The cells were diluted in cell culture medium (RPMI 1640) containing 10% FCS and 300 units/ml human recombinant interleukin 6 (Biochrom, Berlin) and seeded onto 96-well cell culture plates. Afterwards, the cells were selected under HAT medium (medium containing, in addition, hypoxanthine, aminopterin and thymidine). Positive hybridomas were identified by means of FACS analysis of hybridoma supernatents on PBMCs and the hybridoma cells reactive against slan-DCs were recloned several times by limited dilution. The hybridomas MB4 and MB6 resulted from a plurality of more than 100 fusions.

Figure 1:
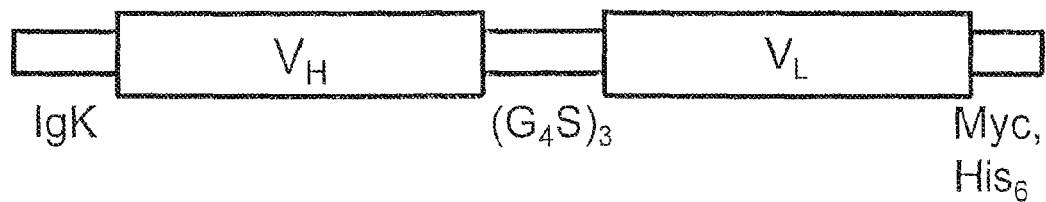
FIG. 1 (A) Schematic configuration of the scFv fragments which contain the variable regions of the heavy chain and light chain of the antibodies MB4 or MB6 according to the invention; (B) binding of the anti-slan antibodies according to the invention MB4 (lower row) and MB6 (upper row) to slan-DC. MB4 and MB6 were tested in the form of monoclonal IgM antibodies (left row) and in the form of an scFv fragment (right row).
Figure 1:
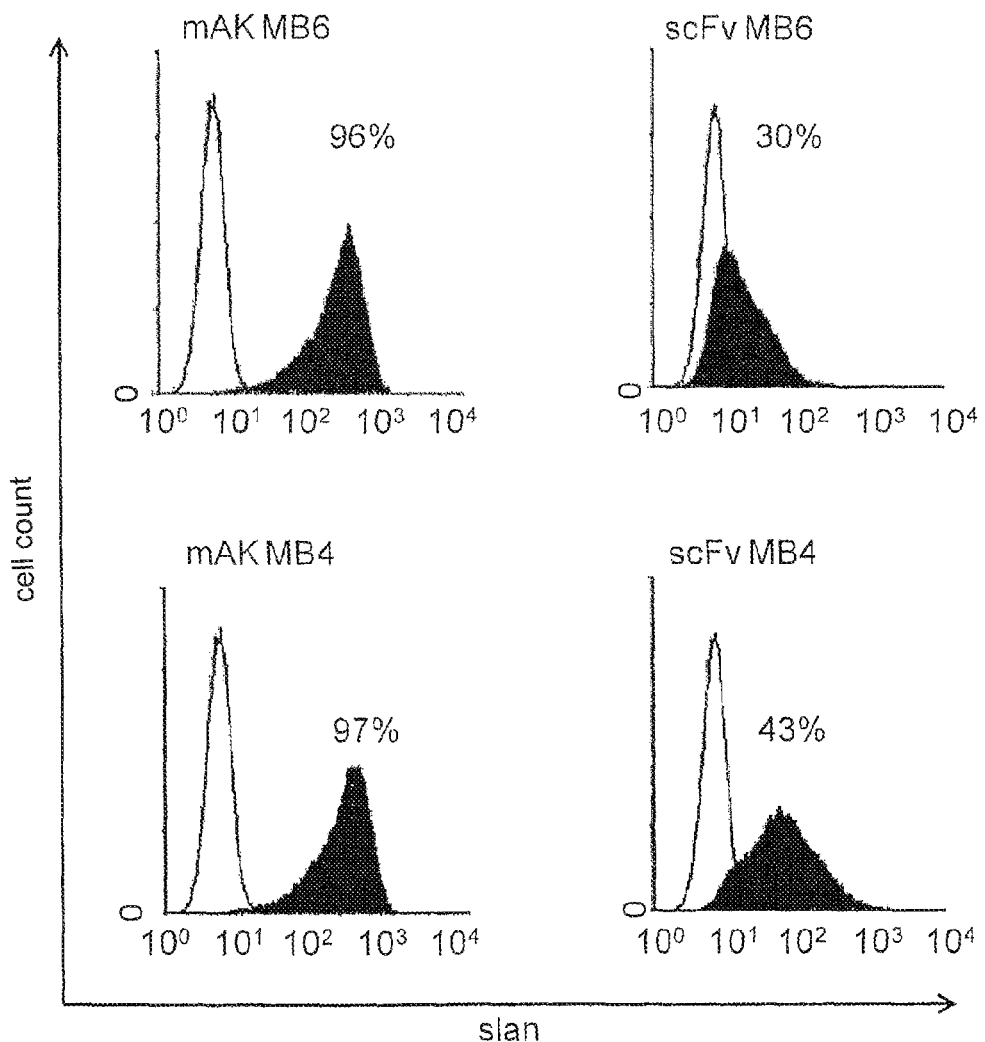

On the basis of the monoclonal IgM antibodies MB4 and MB6 scFv fragments were cloned, schematically shown in FIG. 1 A. In the scFv fragments the variable domains of the monoclonal antibodies MB4 or MB6 are linked in the order "$V_H$-$V_L$" by a flexible glycine serine linker (identified in the illustration by $(G_4S)_3$) with each other. The constructs were cloned into a vector which also codes for a signal sequence which causes the secretion of the antibodies from the cell. Furthermore, the constructs contain C-terminal one c-myc tag (for marking) and a hexahistidine-($His_6$) tag (for the purification of the construct).

The vectors were transfected transiently with lipofectamine 2000 (Invitrogen, Karlsruhe, Germany) into HEK293T cells. After purification of the scFvs of MB4 and MB6 from the cell culture supernatent by nickel affinity chromatography, the scFv and the monoclonal antibodies were tested by FACS analysis in regard to their binding to native slan-DCs. The detection of the scFv was done with anti-c-myc-FITC. The detection of the monoclonal IgM antibodies was done with anti-mouse-IgM-Alexa Fluor® 488 (Invitrogen, Karlsruhe, Germany).

The FACS analysis (FIG. 1B) shows that monoclonal anti-slan antibodies MB6 and MB4 as well as the scFvs that are constructed from their variable domains of the heavy and light chains bind to slan-DCs.

The affinity of the monoclonal antibodies MB4 and MB6 relative to slan DCs is $0.4 \times 10^{-12}$ mol/l and is thus approx. 25 times higher than the affinity of the parallel determined monoclonal anti-s1 slan antibodies DD2 or M-DC8.

Embodiment 2

Providing a Fusion Protein in the Form of a Bispecific Antibody, Containing an Anti-Slan Antibody (DD2)

For providing a composition according to the invention, first a fusion protein was prepared which contains an anti-slan antibody. For this purpose, in the embodiment 2 a fusion protein in the form of a single chain bispecific diabody (scBsDb) was chosen which contains a scFv fragment of the monoclonal anti-slan IgM DD2 as an anti-slan antibody and a further antibody, namely a scFv fragment of the 7B6 antibody. These scBsDb are abbreviated herein schematically also as [DD2-7B6] and comprise an amino acid sequence according to SEQ ID No. 33. A nucleic acid sequence which codes for [DD2-7B6] is cited in SEQ ID No. 32.

The 7B6 antibody binds specifically a peptide structure according to SEQ ID No. 23 and is thus suited for complex formation of the fusion proteins with fusion proteins that contain the peptide structure according to SEQ ID No. 23. One example thereof is cited in embodiment 3.

For cloning [DD2-7B6] the cDNA sequences of the heavy and light chains of DD2 and 7B6 were isolated in form. For this purpose, RNAs were isolated from the respective hybridomas (TriPure reagent from Roche, Mannheim, Germany) and by means of the Advantage RT-for-PCR Kit (Clontech/TaKaRa, Saint-Germain-en-Laye, France) converted in cDNA. The respective cDNAs were amplified with the aid of Advantage-HF 2 Kit PCR (ClontechiTaKaRa, Saint-Germain-en-Laye, France) according to Wang et al. (J. Immunol. Methods 2000, 13, 167-77). The primers according to SEQ ID No. 38 and SEQ ID No. 39 were used for the amplification of the heavy chains of the anti-slan antibody DD2. The primers according to SEQ ID No. 38 and SEQ ID No. 40 were used for the amplification of the heavy chains of the antibody 7B6. The amplification of the light chains for both antibodies was carried out with use of the primers according to SEQ ID No. 41 and SEQ ID No. 42. The resulting PCR products were cloned in pGEM-T easy vector (Promega, Mannheim, Germany) and sequenced. The pGEM-T clones were used as a substrate for SOE PCR for producing the DD2 scFv fragment, wherein the primers according to SEQ ID Nos. 43 to 46 were used. For producing the 7B6-scFv fragment the primers according to SEQ ID Nos. 47 to 50 were used.

To clone scBsDb [DD2-7B6], the heavy and light chains of 7B6 scFv were cloned into the sequence "light chain/heavy chain". In this way, the heavy chain of 7B6 was amplified with the primers according to SEQ ID Nos. 51 and 52 and the light chain of 7B6 with the primers according to SEQ ID Nos. 53 and 54. The light chain was cloned upstream of the heavy chain of 7B6. The 7B6 construct "light chain/heavy chain" was then cloned into DD2 scFv, and scBsDb [DD2-7B6] was formed.

Figure 2:
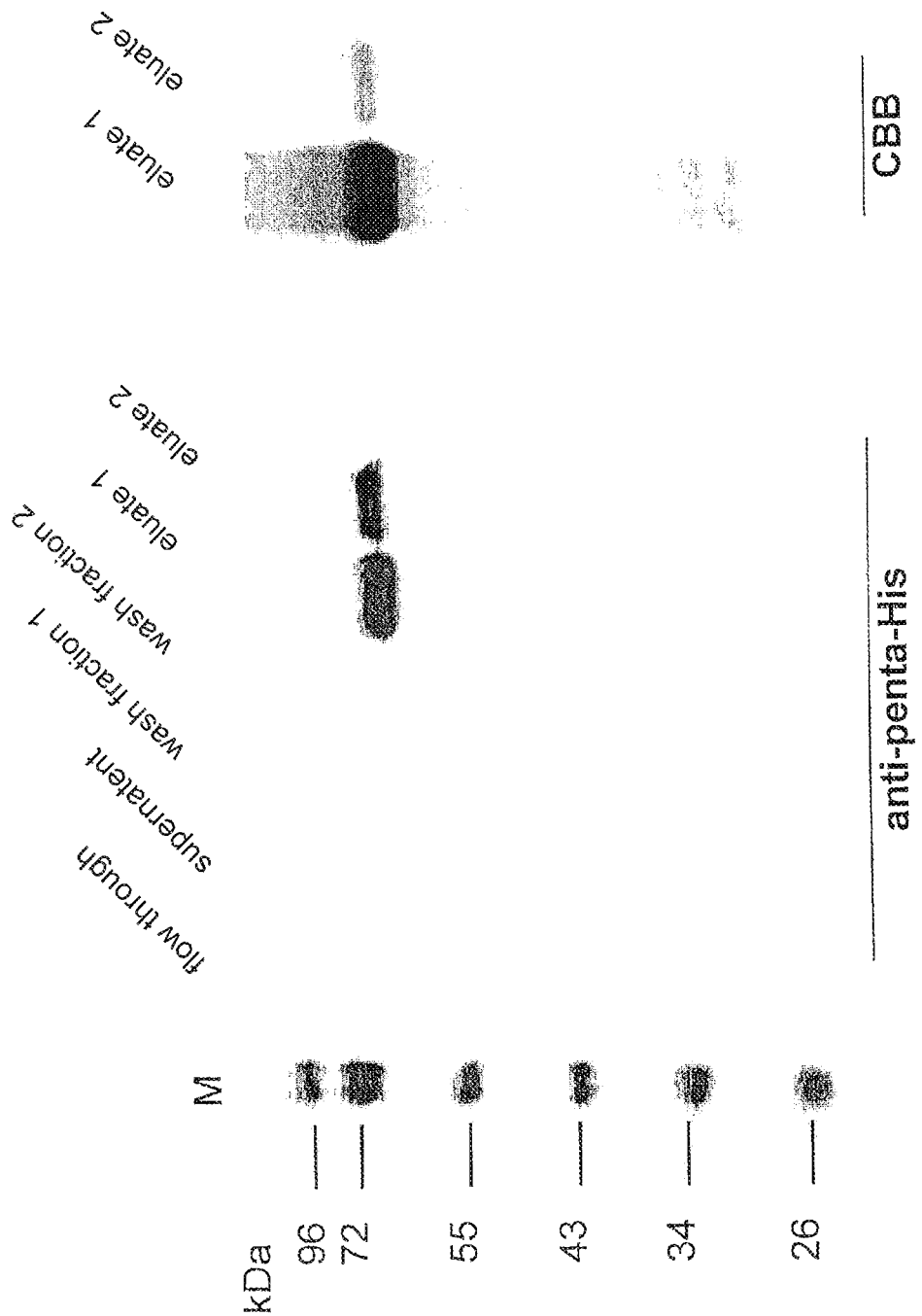
FIG. 2 Immunoblot (A) and SDS PAGE (B) of recombinant bispecific antibodies in the form of scBsDb with an anti-slan DD2 and a 7B6 antibody (herein [DD2-7B6]) after purification. The eluted fractions ("elution 1", "elution 2") contain [DD2-7B6]. References: M . . . marker, supernatant . . . cell culture supernatent, flow trough . . . flow through the column, wash 1, 2 . . . washing fractions, anti-penta HIS . . . monoclonal anti-penta HIS antibody (Qiagen, Hilden, Germany), CBB . . . Coomassie Brilliant Blue.

For the expression of the recombinant antibodies all reading frames of the scFv and also the reading frames of scBsDb [DD2-7B6] were cloned into the vectors pSEC-Tag2B and pcz CFG 5.1. For this purpose, artificial restriction sites for restriction enzymes (either SfiI and NotI or EcoRI and Kpn2I) were inserted by PCT. The formed constructs in pSEC-Tag2B were transiently transfected with lipofectamine 2000 (Invitrogen, Karlsruhe, Germany) into HEK293T cells. The formed constructs in pcz CFG 5.1 were used for producing stably transduced cell lines. Recombinant scFv (7B6 scFv or DD2 scFv) or scBsDb [DD2-7B6] were purified from the cell culture supernatant with the aid of affinity chromatography by Ni-NTA agarose (Qiagen, Hilden, Germany). By SDS-PAGE and immunoblot the purity and stability of scBsDb [DD2-7B6] was determined (FIG. 2).

Embodiment 3

Providing a Fusion Protein Containing a Binding Unit (Peptide E7B6) and an Antigen (an Antigen Peptide from Tetanus Toxin)

As a further component of a composition according to the invention which is used herein in an exemplary fashion in combination with the fusion protein from embodiment 2, a fusion protein was produced, which as a binding unit contains a peptide with the amino acid sequence according to SEQ ID No. 23 (E7B6) and contains as an antigen the green fluorescing protein (GFP). These constructs are abbreviated herein also by [E7B6-7B6-GFP-E7B6](amino acid sequence according to SEQ ID No. 37, nucleic acid sequence according to SEQ ID No. 36). This means that the peptide E7B6 is present three times in the construct. GFP served additionally as a marker and as a spacer molecule.

Further constructs contain, in addition, as an antigen a peptide sequence of the tetanus toxin (herein referred to as TTp). TTp represents an exemplary antigen-containing peptide and was produced by cloning an antigen peptide (herein TTp) derived from tetanus toxin (TT) and containing AA506-526 (according to SEQ ID No. 55) of TT. This construct is abbreviated herein also as [E7B6-TTp-E7B6-GFP-E7B6](amino acid sequence according to SEQ ID No. 35, nucleic acid sequence according to SEQ ID No. 34) and also contain three times the peptide E7B6.

Cloning the linker peptide was carried out as follows: As a template for PCR a vector was used that contained recombinantly the amino acid sequence of the amino acids 311-328 of the human La protein (this is also the sequence of the peptide E7B6 according to SEQ ID No. 23). A new clone with two consecutively positioned E7B6 sequences which are separated by an artificial restriction site for AatII restriction was generated by cloning. Into this restriction site the sequence of the EGFP reading frame was inserted. Afterwards, the nucleic acid sequence of the peptide E7B6 was cloned into this vector so that the construct with three E7B6 peptides and a GFP ([E7B6-E7B6-GFP-E7B6] with amino acid sequence according to SEQ ID No. 37) was generated.

Figure 3:
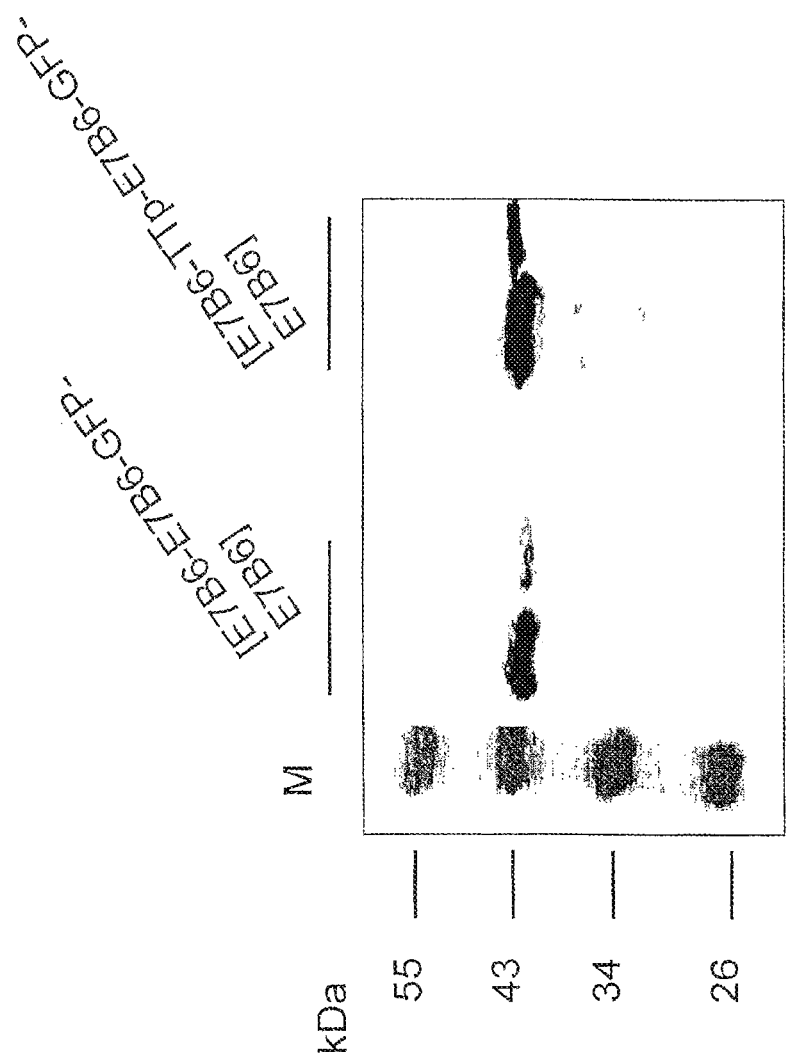
FIG. 3 Immunoblot of fusion proteins of three binding units (E7B6) and at least one antigen (GFP, TTp) after purification. The fusion proteins [E7B6-E7B6-GFP-E7B6] (amino acid sequence according to SEQ ID No. 37) and [E7B6-TTp-E7B6-GFP-E7B6](amino acid sequence according to SEQ ID No. 35) were analyzed.
Figure 4:
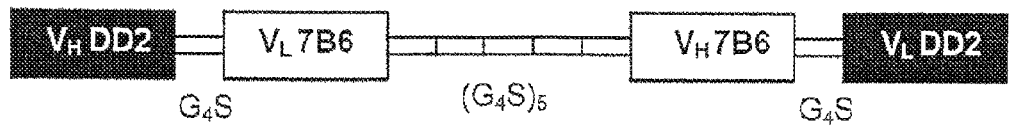
FIG. 4 (A) Schematic illustration of the fusion protein from embodiment 2 [DD2-7B6] according to SEQ ID No. 33; (B) schematic illustration of the constructs of embodiment 3 [E7B6-E7B6-GFP-E7B6](upper schematic, amino acid sequence according to SEQ ID No. 37) and [E7B6-TTp-E7B6-GFP-E7B6](lower schematic, amino acid sequence according to SEQ ID No. 35); (C) schematic illustration of the action mechanism of the therapeutic use of compositions according to the invention. Abbreviations: DC . . . slan dendritic cell (slan-DC), DC Ta . . . slan epitope, anti-DC Ta . . . antibody which is directed against the slan-epitope, E . . . binding unit which is suitable for binding DC activating ligands (identified by the stylized nucleic acid helix), PA . . . antigen. Antigens are transported by fusion proteins that contain anti-slan antibodies, the binding unit, and the antigen to slan-DCs (C, left alternative). Antigens are transported by complexes of fusion proteins to DCs wherein one fusion protein contains the antigen and a further fusion protein contains the anti-slan antibody. Both fusion proteins bind each other (here shown as an antibody bond of an antibody which binds specifically to the binding unit E).
Figure 4:
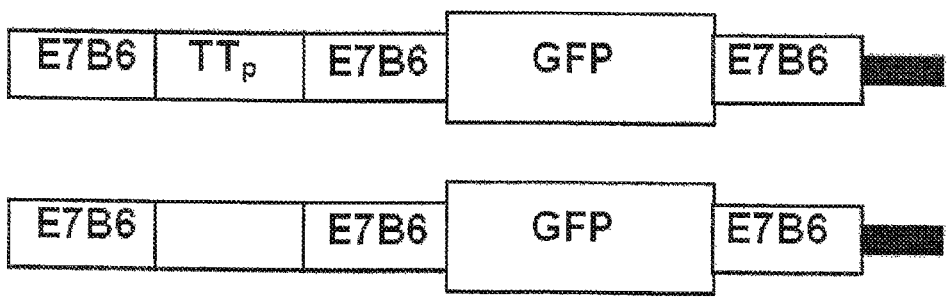
Figure 4:
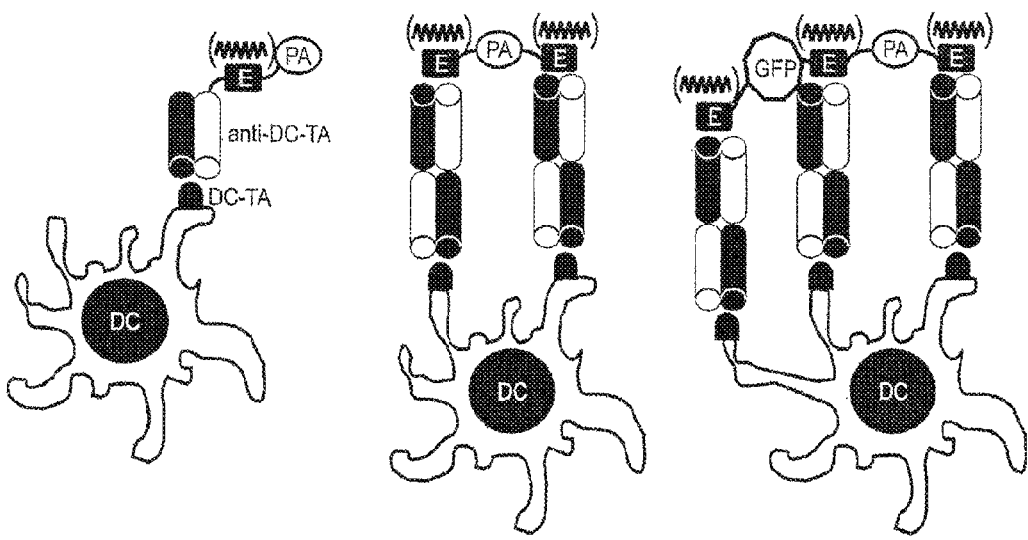

For producing the construct with TTp, the TTp peptide was inserted between the first and second E7B6 elements of the vector for [E7B6-E7B6-GFP-E7B6]. The molecules were recombinantly expressed and purified as described in embodiment 2 (FIG. 3).

The constructs provided by embodiments 2 and 3 were combined with each other so that two compositions according to the invention were formed:
[DD2-7B6] and [E786-E7B6-GFP-E7B6], as well as
[DD2-7B6] and [E7B6-TTp-E7B6-GFP-E7B6].

The antibody 7B6 binds specifically to the peptide 7B6 so that both fusion proteins which are present in the respective composition according to the invention form a complex.

Embodiment 4

Binding of Nucleic Acid to E7B6

Figure 6:
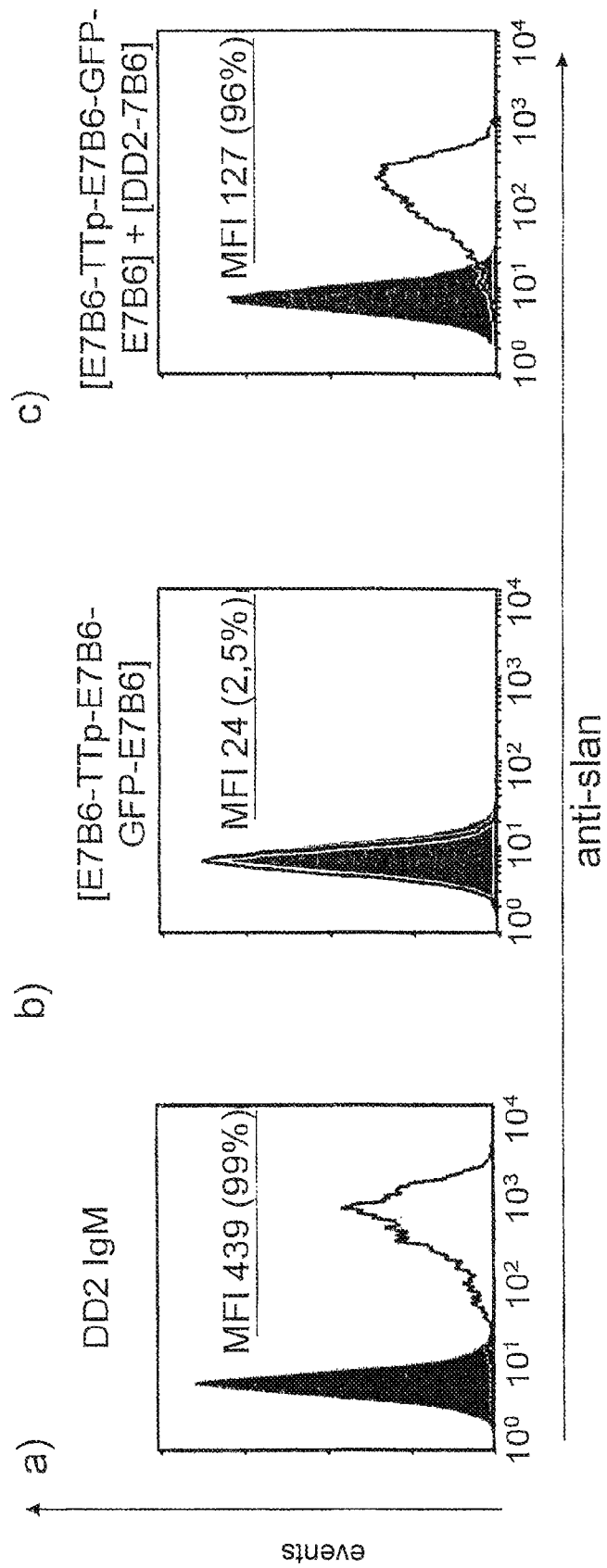
FIG. 6 Binding of a composition according to the invention to slan-positive Jurkat cells. (A) Control: binding of monoclonal anti-slan IgM DD2; (B) control: binding of [E7B6-TTp-E7B6-GFP-E7B6] (amino acid sequence according to SEQ ID No. 35) without anti-slan antibody; (C) composition according to the invention containing a fusion protein with anti-slan antibody [DD2-E7B6] (according to SEQ ID No. 33) and a fusion protein with two antigens [E7B6-TTp-E7B6-GFP-E7B6] (according to SEQ ID No. 35), wherein the fusion proteins are present as a complex because they are linked to each other by binding of 7B6 and E7B6 (MFI . . . median fluorescence intensity).
Figure 7:
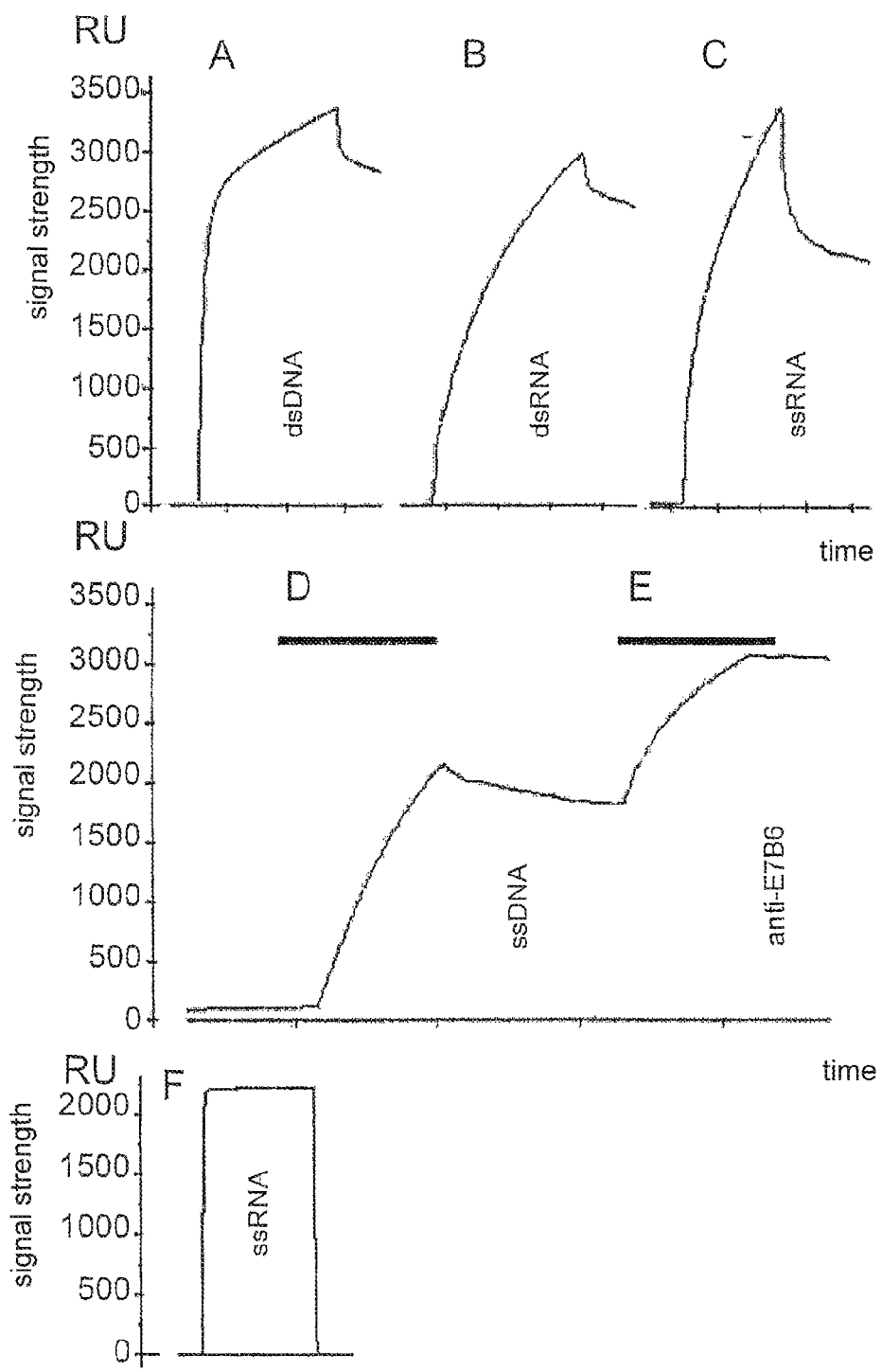
FIG. 7 (A-F) Complex formation with nucleic acids by fusion proteins according to the invention with a peptide according to SEQ ID No. 23 (E7B6) determined by complex formation on SPR chips. Complex formation with (A) dsDNA, (B) dsRNA, (C) ssRNA, (D) ssDNA. (E) Binding of a specific antibody after complex formation with nucleic acid. (F) Comparative example: binding of a fusion protein with Gly Ser linker on ssRNA. Figure legend: Response . . . Intensity of binding in RU (response units, binding units), time . . . time.

The peptide E7B6 which is contained in the fusion protein of embodiment 3 binds to nucleic acids. For detection, the nucleic acid bond was determined by means of surface plasmon resonance (SPR) (FIG. 7 A-E). For this purpose, different nucleic acids (dsDNA, ssDNA, dsRNA, ssRNA) were coupled to a commercially available SPR CHIP and contacted with fusion proteins which contain a peptide E7B6 and fusion proteins peptide E7B6 (comparative example). Fusion proteins with E7B6 bind with high affinity to nucleic acids of the type dsDNA (FIG. 7 A), ssDNA (FIG. 7 D), dsRNA (FIG. 7 B) and with lower affinity ssRNA (FIG. 7 C). Fusion proteins without E7B6 (FIG. 6 F) do not bind to nucleic acids. Binding to nucleic acids does not impair binding of specific antibodies to the linker peptide. FIG. 7 E shows binding of the 7B6 antibody (monoclonal IgG1) which binds specifically to the peptide E7B6 after binding to nucleic acids. The shortest bound nucleic acid was 15-mer ssDNA.

Embodiment 5

Figure 5:
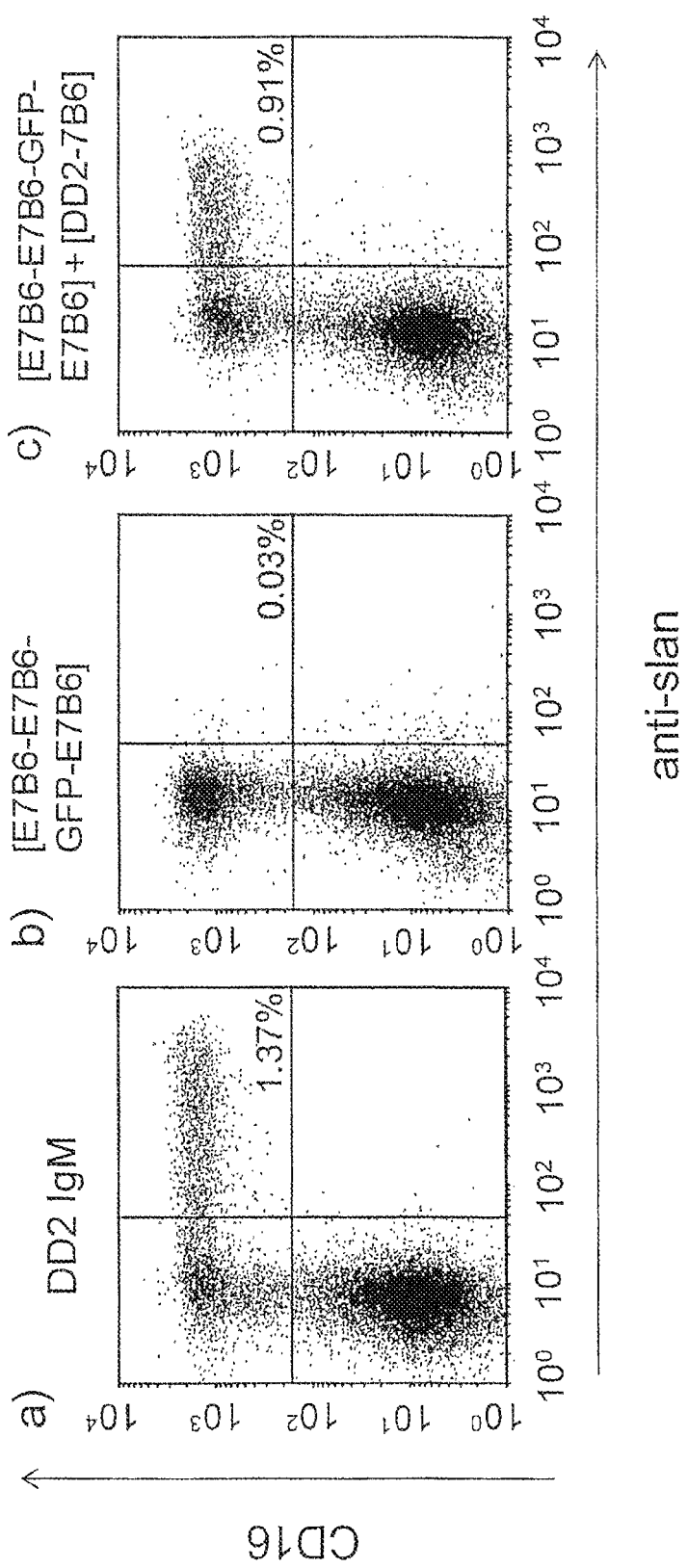
FIG. 5 Binding of a composition according to the invention to native human CD16$^+$/slan$^+$ slan-DC. (A) Control: Proportion of the slan-DCs in native PBMC, detected with a monoclonal anti-slan IgM (DD2); (B) control: [E7B6-E7B6-GFP-E7B6](amino acid sequence according to SEQ ID No. 37) alone without anti-slan antibody; (C) composition according to the invention containing a fusion protein with anti-slan antibody [DD2-E7B6] (according to SEQ ID No. 33) and a fusion protein with antigen [E7B6-E7B6-GFP-E7B6](amino acid sequence according to SEQ ID No. 37), wherein the fusion proteins are present as a complex because they are linked to each other by binding of 7B6 and E7B6 (MFI . . . median fluorescence intensity).

Binding of a Composition According to the Invention with [DD2-7B6] and [E7B6-E7B6-GFP-E7B6] to Native Slan-DCs In the experiment, human PBMCs were used and analyzed after staining with fluorescence-marked antibody by means of FACS analysis. PBMCs contain slan-DCs so that binding of a complex of [DD2-7B6] and [E7B6-E7B6-GFP-E7B6] was tested on slan-DCs. As a comparative example he slan-DCs with monoclonal anti-slan IgM DD2 (FIG. 5a) and [E7B6-E7B6-GFP-E7B6] without [DD2-7B6] were stained (FIG. 5b). It is evident that [E7B6-E7B6-GFP-E7B6] alone does not bind to slan-DCs. Compositions according to the invention from [DD2-7B6] and [E7B6-

E7B6-GFP-E7B6] bind to slan-DCs (FIG. 5c). In each case, co-staining of the examined proteins with anti-CD16 was carried out.

Embodiment 6

Binding of a Composition According to the Invention with [DD2-7B6] and [E7B6-TTp-E7B6-GFP-E7B6] Slan+ Jurkat Cells In the experiment, as an in vitro model for slan-positive cells a Jurkat cell line (herein "slan+Jurkat") was used that expressed the slan epitope on the surface (Schäkel et al., Immunity, 2002, 17, 289-301). Binding of the composition according to the invention of [DD2-7B6] and [E7B6-TTp-E7B6-GFP-E7B6], which are present in the composition as a complex, was determined by FACS analysis.

As a comparative example, the slan+ Jurkat with monoclonal anti-slan IgM DD2 (FIG. 6a) and [E7B6-TTp-E7B6-GFP-E7B6] without [DD2-7B6] were stained (FIG. 6b). It is evident that [E7B6-TTp-E7B6-GFP-E7B6] alone does not bind to slan+ Jurkat. In FIG. 6C, the FACS staining of slan+ Jurkat with a complex of [DD2-7B6] and [E7B6-TTp-E7B6-GFP-E7B6] is illustrated. Binding of the complex to slan+ Jurkat was successful and was almost as effective as binding of the monoclonal anti-slan IgM DD2 antibody used as a comparative example.

Embodiment 7

Comparison of Binding of the scFv Fragments of DD2, MB4 and MB6 to Slan-DCs scFv fragments of the anti-slan antibodies MB4 and MB6 according to the invention (according to embodiment 1) and an scFv fragment of the anti-slan antibody DD2 (as contained in the bispecific antibody according to embodiment 2) were provided.

By FACS analysis the scFv fragments were tested in regard to binding to the slan epitope. The detection of scFv occurred with anti-c-myc FITC (for MB4 and MB6) and with anti-His Alexa488 ® for scFv of DD2.

The FACS analysis (FIG. 1B) shows that monoclonal anti-slan antibodies MB6 and MB4 as well as scFvs constructed from their variable domains of the heavy and light chains bind very well to slan-DCs.

Figure 8:
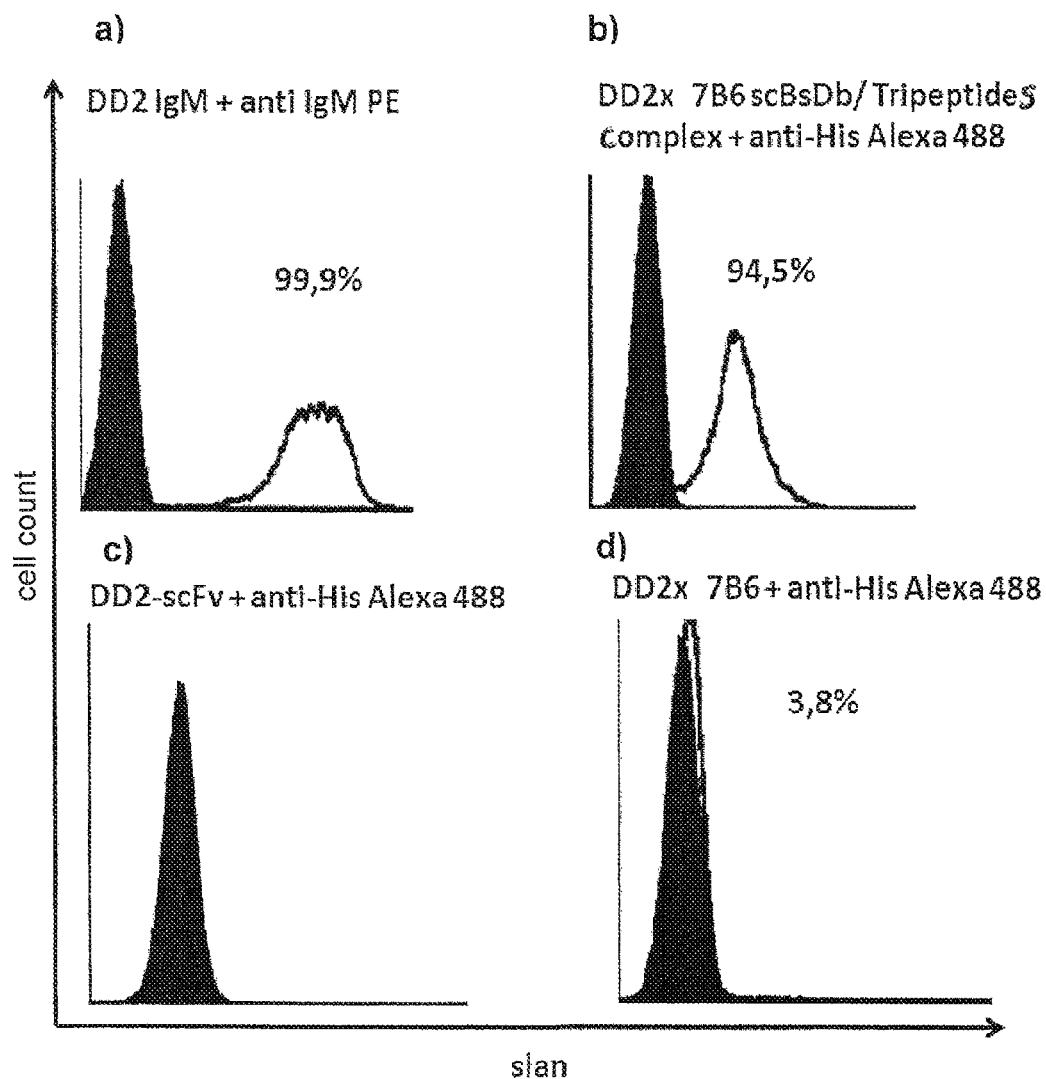
FIG. 8 Binding of scFv of DD2 to slan-positive Jurkat cells determined by FACS analysis. (a) Control: binding of the monoclonal IgM antibody DD2, (b) binding of a composition according to the invention according to embodiments 2 and 3 ([DD2-7B6] and [E7B6-E7B6-GFP-E7B6]; identified in the illustration as "DD2x7B6 scBsDb/tripeptide complex"), (c) binding of DD2 scFv fragment, (e) control: binding of the bispecific antibody of embodiment 2 [DD2-7B6].

The scFv of the anti-slan antibody DD2 bind in monovalent form badly to the slan epitope (FIG. 8c). The binding capability of the DD2 antibodies is reconstituted by providing the scFv fragments in a composition according to the invention, for example, according to the embodiments 5 and 6 (FIG. 8B, in the form of a composition according to the invention with [DD2-7B6] and [E7B6-E7B6-GFP-E7B6] according to embodiments 2 and 3). The shows that, when furnished in a composition according to the invention, antibody fragments, in particular scFv, that have a low affinity to the specific antigen are suitable also. The advantages of the pentameric IgM antibodies can thus be transferred onto the composition according to the invention while the disadvantages of the bulky IgM antibody, in particular the difficult handling due to their size, are overcome.

Embodiment 8

Activation of Slan-DCs after Targeted Transport of a Co-Stimulus (TLR Ligands) with the Aid of a Composition According to the Invention with [DD2-7B6] and [E7B6-E7B6-GFP-E7B6]

For the transport of nucleic acid from *Escherichia coli* (an activating co-stimulus which binds to different Toll-like receptors) to slan-DCs in an in vitro experiment a composition according to the invention was used, comprising
 the anti-slan antibody: [DD2-7B6](amino acid sequence according to SEQ ID No. 33, nucleic acid sequence according to SEQ ID No. 32) and
 the oligopeptide containing three E7B6 binding units: [E7B6-E7B6-GFP-E7B6](amino acid sequence according to SEQ ID No. 37, nucleic acid sequence according to SEQ ID No. 36).

The activation of the slan-DCs was determined by the detection of the TNF-α concentration in the cell culture supernatent. This was determined by ELISA.

The following procedure was used:

Nucleic acids were isolated from total extracts of *E. coli*. For loading the oligopeptide [E7B6-E7B6-GFP-E7B6] containing the binding unit "E7B6" that binds the nucleic acid, 1 mg of the oligopeptide [E7B6-E7B6-GFP-E7B6], respectively, was incubated with 0.1 mg, respectively, of the nucleic acid preparation obtained from *E. coli* for 1 hr. at room temperature. A complex in which nucleic acid is bound to [E7B6-E7B6-GFP-E7B6] is obtainable in this way (herein NA-[E7B6-E7B6-GFP-E7B6]). As a control, a sample of the oligopeptide NA-[E7B6-E7B6-GFP-E7B6] that is loaded with nucleic acid was treated with a mixture of RNAseA, TI and DNAseI (incubation over night). The nucleic acid bound to the oligopeptide is thereby digested so that only the oligopeptide should remain. The sample digested with nucleases is referred to in the following as NA*-[E7BB-E7B6-GFP-E7B6]. Afterwards, both samples [E7B6-E7B6-GFP-E7B6] and NA*-[E7B6-E7B6-GFP-E7B6] were purified again by means of a nickel-affinity column, and digested and unbound nucleic acid components were separated from the oligopeptide in this way.

Afterwards, bispecific anti-slan antibody [DD2-7B6] was added in a molar ratio of 1:3 (oligopeptide to bispecific antibodies), respectively, to both samples NA-[E7B6-E7B6-GFP-E7B6] and NA*-[E7B6-E7B6-GFP-E7B6] in separate batches followed by incubation for 2 hrs at room temperature. In this context, complex formation occurs between the respective oligopeptide with the E7B6 domain and the bispecific antibody [DD2-7B6] which binds with the 7B6 part to the E7B6 peptide. The complexes available thereby are referred to herein in a simplified way as follows:
 complex NA-[E7B6-E7B6-GFP-E7B6] and [DD2-7B6]: NA-DD2
 complex NA*-[E7B6-E7B6-GFP-E7B6] and [DD2-7B6]: NA*-DD2

In into vitro experiments, freshly isolated slan-DCs (in each case 1.4×10⁶ DCs) were added to aliquots of the complexes NA-DD2 (according to the invention) and NA*-DD2 (negative control) (containing in each case 2.8 nmol of the bispecific antibody [DD2-7B6]) followed by incubation over night. As further controls, under identical conditions, a complex of [E7B6-E7B6-GFP-E7B6](without nucleic acid loading, without digestion) with [DD2-7B6] was used (negative control, the complex is referred to as *-DD2 herein). Furthermore, slan-DC:s were stimulated with the TLR4 ligand LPS (without complex) under otherwise identical conditions, which leads to an activation of the slan-DCs (positive control). Afterwards, the cell culture supernatent was removed and analyzed by means of TNF-α.

Figure 9:
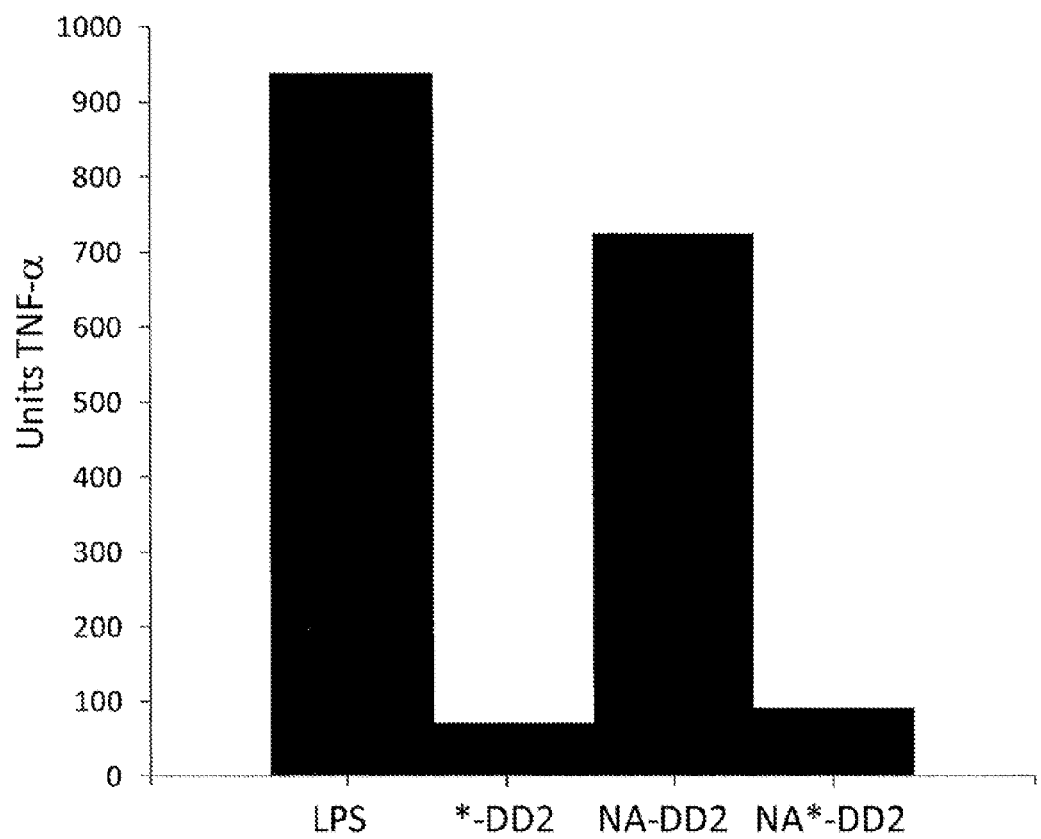
FIG. 9 TNFα production of slan-DCs after TLR-dependent activation in vitro determined by TNFα-ELISA. To freshly isolated slan-DCs the following samples were added: LPS (positive control), *-DD2 (negative control), NA-DD2 (composition according to the invention containing oligopeptide [E7B6-E7B6-GFP-E7B6] loaded with nucleic acid from E. coli and [DD2-7B6]) as well as NA*-DD2 (negative control).

FIG. 9 shows the results of the anti-TNFα ELISA. The composition according to the invention is suitable for transporting co-stimuli, like the Toll-like receptor ligands (nucleic acids) tested here, to slan-DCs which results in an activation of the slan-DCs.

What is claimed is:

1. A composition comprising
   a) at least one anti-slan antibody which binds specifically to 6-sulfo N-acetyl lactosamine (6-suldo LacNAc) of P-selectin glycoprotein ligand 1 (PSGL-1) on the surface of human dendritic cells,
   b) at least one binding unit which binds to a co-stimulus, wherein the co-stimulus binds to a receptor on dendritic cells that is specific for the co-stimulus, wherein the co-stimulus is selected from nucleic acid Toll-receptor ligands (TLR ligands) that cause the modulation of said dendritic cells, wherein the binding unit is a nucleic acid binding peptide that comprises the amino acid sequence EKEALKKIIEDQQESLNK (SEQ ID No. 23),
   c) at least one antigen, and
   d) a further binding unit that is an antibody which binds the nucleic acid binding peptide specifically.

2. The composition according to claim 1, wherein the anti-slan antibody and the binding unit are present as a fusion protein or the antigen and the binding unit are present as a fusion protein.

3. The composition according to claim 1, wherein the binding unit and/or the further binding unit is bound to the anti-slan antibody and/or the antigen by a covalent bond.

4. The composition according to claim 3, wherein the covalent bond is a peptide bond.

5. The composition according to claim 1, wherein
   the anti-scan antibody and the binding unit are present as a fusion protein and the further binding unit and the antigen are present as a fusion protein, or
   the anti-clan antibody and the further binding unit are present as a fusion protein and the antigen and the binding unit are present as a fusion protein.

6. The composition according to claim 1, wherein the TLR ligand is selected from the group consisting of ssRNA, dsRNA, and unmethylated CpG DNA.

7. The composition according to claim 6, wherein the antibody which binds the nucleic acid binding peptide specifically comprises the following CDR regions:
   variable region of the heavy chain ($V_H$): CDR1 SEQ ID No. 26, CDR2 SEQ ID No. 27, CDR3 SEQ ID No. 28, and
   variable region of the light chain ($V_L$): CDR1 SEQ ID No. 29, CDR2 SEQ ID No. 30, CDR3 SEQ ID No. 31.

8. The composition according to claim 1, wherein the anti-slan antibody comprises regions determining complementarity (complementarity determining regions, CDRs), wherein the CDRs comprise the following amino acid sequences:

a) variable region of the heavy chain ($V_H$):

```
                              (SEQ ID No. 1)
CDR1 TYGVH, (SEQ ID No. 2)
CDR2 VIWSGGGTDFNVAFXS, wherein X is selected from M, L, F, or I, (SEQ ID No. 5)
CDR3 RTTNDGNYAFAY,
and
``` b) variable region of the light chain ($V_L$):

```
                              (SEQ ID No. 6)
CDR1 RSSQNILHSDGXTYLE, wherein X is selected from S, T, N, Q, H, K or R, (SEQ ID No. 9)
CDR2 KVSNRFS
and (SEQ ID No. 10)
CDR3 FQGSHVPWT.
```

9. The composition according to claim 8, wherein the anti-scan antibody has a humanized structure.

10. The composition according to claim 8, wherein the CDRs of the anti-slan antibodies comprise the following amino acid sequences:

CDR2 of the variable region of the heavy chain comprising the amino acid sequence according to SEQ ID No. 3 and CDR1 of the variable region of the light chain comprising the amino acid sequence according to SEQ ID No 7, or CDR2 of the variable region of the heavy chain comprising the amino acid sequence according to SEQ ID No. 4 and CDR1 of the variable region of the light chain comprising the amino acid sequence according to SEQ ID No 8.

11. The composition according to claim 10, wherein the anti-slan antibody comprises the following structure:

variable region of the heavy chain according to SEQ ID No. 12 and variable region of the light chain according to SEQ ID No. 14, or variable region of the heavy chain according to SEQ ID No. 16 and variable region of the light chain according to SEQ ID No. 18.

12. The composition according to claim 1, wherein the antigen is a tumor antigen.

13. A pharmaceutical kit, containing a composition according to claim 1 and a TLR ligand that effects the activation of human dendritic cells in association with a pharmaceutically suitable diluent or carrier, optionally in a form suitable for intravenous administration.

14. The pharmaceutical kit according to claim 13 for the therapeutic treatment of tumor illnesses, wherein the antigen is a tumor antigen.

* * * * *